US010468126B1

(12) United States Patent
Harding et al.

(10) Patent No.: US 10,468,126 B1
(45) Date of Patent: Nov. 5, 2019

(54) CLINICAL ACTIVITY NETWORK GENERATION

(71) Applicant: MULTISCALE HEALTH NETWORKS LLC, Seattle, WA (US)

(72) Inventors: James A. Harding, Issaquah, WA (US); Mark W. Bowers, Langley, WA (US); Alejandro G. Carrillo, Seattle, WA (US); Scott Thibault, Burlington, VT (US)

(73) Assignee: MULTISCALE HEALTH NETWORKS, LLC., Seattle, WA (US)

( * ) Notice: Subject to any disclaimer, the term of this patent is extended or adjusted under 35 U.S.C. 154(b) by 1041 days.

(21) Appl. No.: 14/829,446

(22) Filed: Aug. 18, 2015

Related U.S. Application Data

(63) Continuation-in-part of application No. 14/693,147, filed on Apr. 22, 2015, and a continuation-in-part of application No. 14/463,542, filed on Aug. 19, 2014.

(60) Provisional application No. 62/039,059, filed on Aug. 19, 2014.

(51) Int. Cl.
*G16H 10/60* (2018.01)
*G06F 17/27* (2006.01)
*G06F 16/36* (2019.01)

(52) U.S. Cl.
CPC ........... *G16H 10/60* (2018.01); *G06F 16/367* (2019.01); *G06F 17/2705* (2013.01)

(58) Field of Classification Search
CPC ................ G16H 10/60; G06F 17/2705; G06F 17/30734
See application file for complete search history.

(56) References Cited

U.S. PATENT DOCUMENTS

| 6,374,262 | B1 | 4/2002 | Kodama | |
|---|---|---|---|---|
| 7,082,435 | B1 | 7/2006 | Guzman et al. | |
| 2002/0016718 | A1 | 2/2002 | Rothschild et al. | |
| 2005/0137910 | A1 | 6/2005 | Rao et al. | |
| 2005/0251540 | A1 | 11/2005 | Sim-Tang | |
| 2010/0198622 | A1* | 8/2010 | Gajic | G06Q 50/22 705/3 |
| 2011/0153364 | A1* | 6/2011 | Kerr | G06Q 50/22 705/3 |
| 2011/0246876 | A1 | 10/2011 | Chutani et al. | |
| 2011/0288877 | A1* | 11/2011 | Ofek | G06Q 10/10 705/2 |

(Continued)

OTHER PUBLICATIONS

The theory of B-trees published on Dec. 15, 2002.

(Continued)

*Primary Examiner* — Linh Giang Le
(74) *Attorney, Agent, or Firm* — Lowe Graham Jones PLLC

(57) ABSTRACT

Clinical activity network applications are described. Some embodiments provide an Operational Intelligence Platform ("OIP") that is configured to generate a clinical activity network that uniformly represents actions and data updates occurring in a source healthcare system. Each clinical activity instance associates an action (or activity) with a context, a time, a user, and a patient or other subject. By analyzing collections of clinical activity instances, applications can identify patterns, processes, and relationships within the healthcare setting that would not necessarily be detectable when analyzing data from a single source, such as the source customer database.

20 Claims, 16 Drawing Sheets

(56) References Cited

U.S. PATENT DOCUMENTS

2012/0216179 A1    8/2012   Sharma et al.
2013/0036090 A1    2/2013   Akiyama
2013/0054693 A1    2/2013   Chennamadhavuni
2013/0346725 A1   12/2013   Lomet et al.

OTHER PUBLICATIONS

E.F. Codd, "A Relational Model of Data of Large Shared Data Banks", Communications of the ACM, vol. 13, No. 6, p. 377-387, Jun. 1970.

* cited by examiner

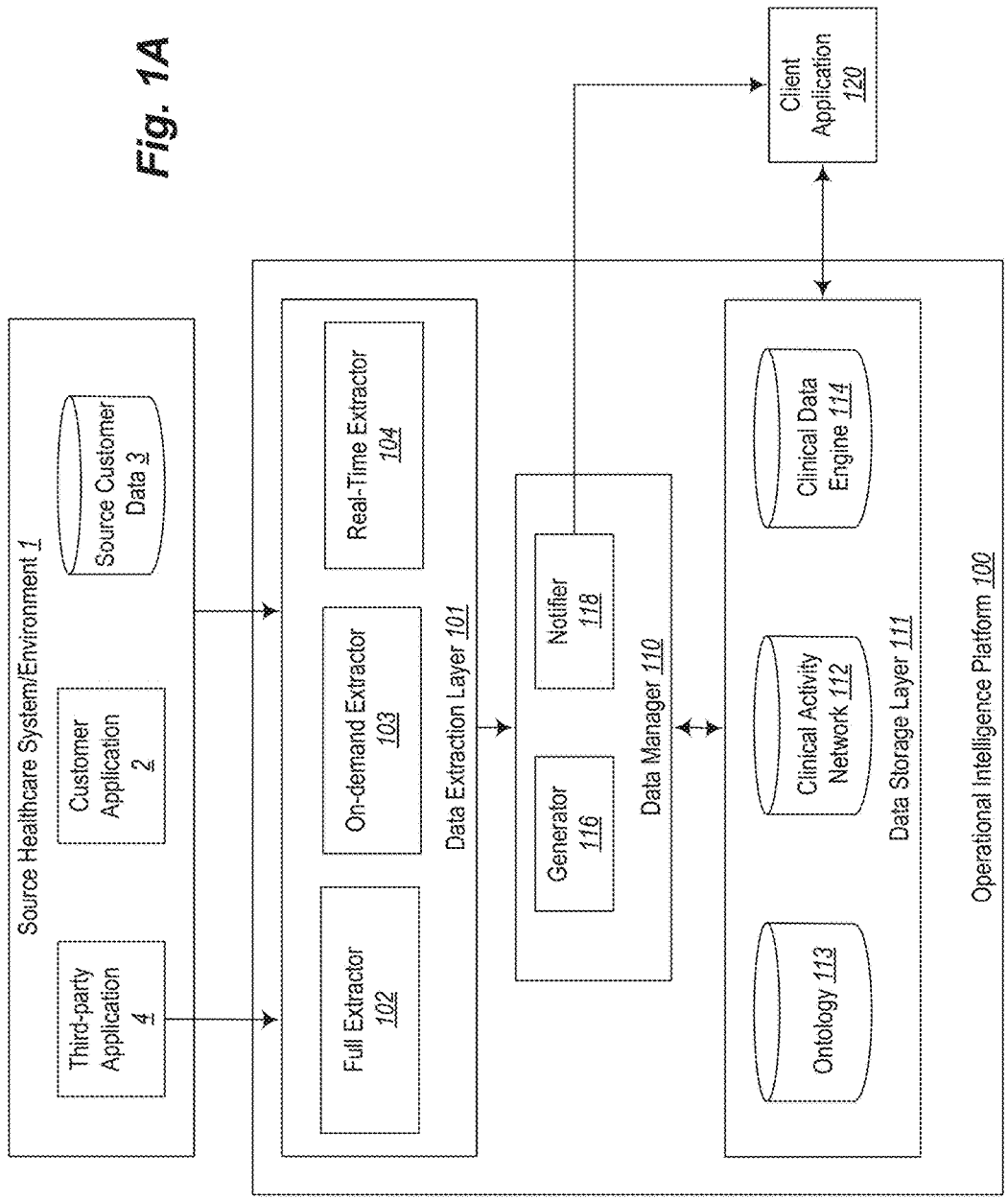

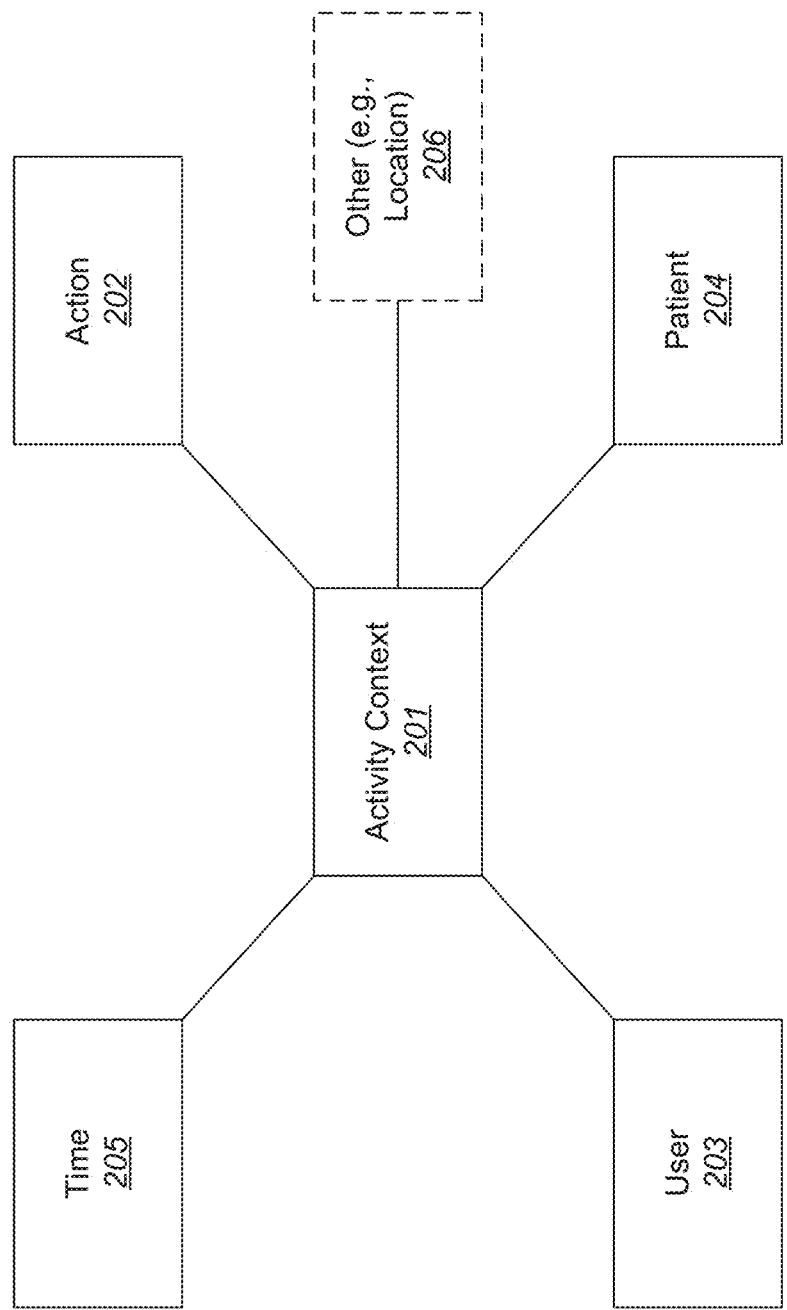

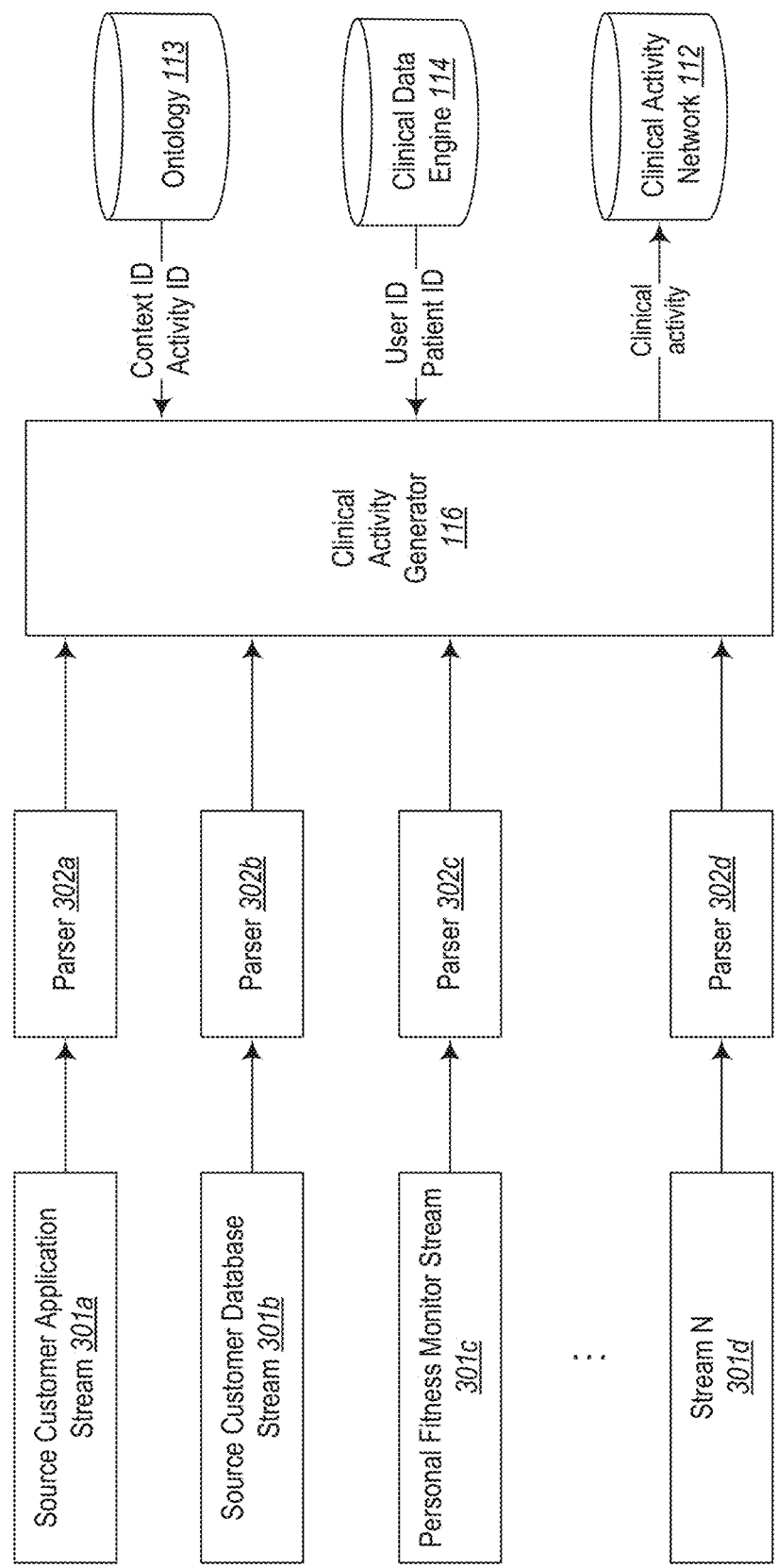

*Fig. 4A*

| Activity Type | Name | Definition | Pattern Specification or Example |
|---|---|---|---|
| Context | PatientChart | The activity of moving to/opening the patient charting form | PatientChart(Z59777) |
| Action | Enter Vitals | Enter various vital data for the patient | EV.PatientChart(Z59777, 99,129/89, 22) |
| Action | Enter Note | Update a note about the patient visit | Note.PatientChart(Z59777,"Patient responding well to meds") |
| Context | Floor Trackboard | The activity of moving to/opening the track board form for the Floor | FTBoard() |
| Action | EnterBed | Enter the bed location for a floor patient | EnterBed.FTBoard(Z59777, BA10) |
| Action | Exit Activity | User leaves a context and goes to another context (or just exist without going to another context) | Exit.FTBoard |

*Fig. 4B*

| CAN ID | Receipt Time | User ID | Activity ID | Subj. Type ID | Subject | Content |
|---|---|---|---|---|---|---|
| --- | TIME | USER | ACTIVITY | | PATIENT | |
| 13288 | 08/02/14 @3:27:14am | MSHN101 | AC2501 | 1 | Z59777 | PatientChart(Z59777) |
| ... | | | | | | |
| 13365 | 08/03/14 @5:28:11pm | MSHN101 | AA902 | 1 | Z59777 | EV.PatientChart(Z59777,99,129/89, 22) |
| ... | | | | | | |

*Fig. 4C*

| CAN ID | Receipt Time | User ID | Activity ID | Subj. ID | Content |
|---|---|---|---|---|---|
| --- | TIME | USER | ACTIVITY | PATIENT | |
| 13288 | 08/02/14 @3:27:14am | MSHN101 | AC2501 | Z59777 | PatientChart(Z59777) |
| 13365 | 08/03/14 @5:28:11pm | MSHN101 | AA902 | Z59777 | EV.PatientChart(Z59777, 99,129/89, 22) |

*Fig. 4D*

| Activity ID | Context ActivityID | Activity Name | Definition | Pattern Example |
|---|---|---|---|---|
| AC501 | -- | PatientChart | The activity of moving to/opening the patient charting form | PatientChart(Z59777) |
| AA902 | AC501 | EV | Enter various vital data for the patient | EV.PatientChart(Z59777,99,129/89, 22) |
| AA877 | AC501 | Note | Update a note about the patient visit | |
| AC728 | -- | FTBoard | The activity of moving to/opening the track board form for the Floor | FTBoard() |
| AA310 | AC728 | EnterBed | Enter the bed location for a floor patient | EnterBed.FTBoard(Z59777,BA10) |
| AA791 | AC728 | Exit Activity | User leaves a context and goes to another context (or just exist without going to another context) | Exit.FTBoard |

*Fig. 4E*

| CAN ID | Receipt Time | User ID | Activity ID | Subject | Content |
|---|---|---|---|---|---|
| --- | TIME | USER | ACTIVITY | PATIENT | |
| 13288 | 08/02/14 @3:27:14am | MSHN101 | AC2501 | Z59777 | PatientChart(Z59777) |
| ... | | | | | |
| 13299 | 08/02/14 @9:44:14pm | MSHN122 | AA310 | Z59777 | EnterBed.FTBoard(Z59777,BA10) |
| ... | | | | | |
| 13365 | 08/03/14 @5:28:11pm | MSHN101 | AA902 | Z59777 | EV.PatientChart(Z59777,99,129/89, 22) |
| ... | | | | | |
| 13384 | 08/03/14 @5:31:22pm | MSHN101 | AC728 | Z59777 | FTBoard() |
| 13385 | 08/03/14 @5:31:34pm | MSHN101 | AA310 | Z59777 | EnterBed.FTBoard(Z59777,BC12) |

*Fig. 4F*

| CAN ID | Receipt Time | User ID | Activity ID | Subject | Content |
|---|---|---|---|---|---|
| -- | TIME | USER | ACTIVITY | PATIENT | |
| ... | | | | | |
| 14088 | 08/04/14 @1:07:10am | Z59777 | AC2501 | Z59777 | Vitals { {BT : 98.5}, {RR:29} } |
| ... | | | | | |

| CAN ID | ReceiptTime | UserID | ActivityID | Subject | Content |
|---|---|---|---|---|---|
| -- | TIME | USER | ACTIVITY | PATIENT | |
| ... | | | | | |
| 13289 | 08/02/14 @3:27:15am | MSHN101 | UNKNOWN | Z59777 | SLevel.FTBoard(Z59777,10) |
| ... | | | | | |

| Element | Description | Example |
|---|---|---|
| UserID | This is the clinical activity network User ID. In some cases, a user ID is provided by the healthcare application, which can be mapped to a user ID stored in the clinical activity network. In other cases, a process identifier is stored in a healthcare database system (e.g., along with an update to a journal file), which can be mapped to a user ID stored in the clinical activity network. | MSHN1010 |
| Activity | This is a pattern for an Activity. An Activity pattern is unique for each FeedID. | PatientChart(Z59777) |
| ReceiptTime | The time the parser recognizes the pattern and created the record. | UTC TimeStamp |
| FeedID | Each feed type will have a unique ID. | FT01 |

*Fig. 5*

| Item | Key | Value |
|---|---|---|
| 1 | ^ENU("FSD","99500000","1000","0") | 101\|101\|101\|101\|101\|101\|101\|101\|101\|101 |
| 2 | ^ENU("FSD","99500000","1000","101") | 6\|5477659371\[PDT\|5477660271 \[PDT\|RJT1\]\|98.20004 |
| 3 | ^ER1("INP","99322190","60","99999","1") | 99222190 |
| 4 | ^EX("INP","60","99222190","99322190") | 1 |
| 5 | ^ENU("FSD","99500000","1000","0") | 102\|102\|102\|102\|102\|102\|102\|102\|102\|102 |
| 6 | ^ENU("FSD","99500000","1000","102") | 2204\|5477659371\[PDT\|5477660271 \[PDT\|RJT1\]\|116 |

Fig. 6C

6300: The process of 6100, wherein the generating, based on the source event and an activity ontology, a clinical activity instance includes:

6301: Parsing the received source event to generate an activity pattern

6302: Matching the generated activity pattern against the activity ontology

Fig. 6D

6400: The process of 6100, wherein the generating, based on the source event and an activity ontology, a clinical activity instance includes:

6401: Determining the user based on information external to the source event

Fig. 6E

6500: The process of 6400, wherein the determining the user based on information external to the source event includes:

6501: Tracking log in and log out events

6502: Generating an association between users and process identifiers based on the tracked events

6503: Determining the user by looking up the process identifier in the generated association

Fig. 6F

6600: The process of 6400, wherein the determining the user based on information external to the source event includes:

6601: Determining a process identifier associated with the source event

6602: Determining the user by looking up the process identifier in an association between users and process identifiers

Fig. 6G

6700: The process of 6100, further comprising:

6701: Determining the action based on data content of the source event

Fig. 6H

6800: The process of 6100, further comprising:

6801: Receiving a second source event

6802: Determining at least one portion of a clinical activity instance based on the second source event 6803: Receiving a third source event after the second source event 6804: Determining remaining fields of the clinical activity instance based on the third source event

Fig. 6I

6900: The process of 6100, further comprising:

6901: Determining a location associated with the source event

CLINICAL ACTIVITY NETWORK GENERATION

PRIORITY CLAIM

This application is a continuation-in-part of U.S. patent application Ser. No. 14/693,147, filed Apr. 22, 2015, which is a continuation-in-part of U.S. patent application Ser. No. 14/463,542, filed Aug. 19, 2014. This application claims priority to U.S. Provisional Patent Application No. 62/039, 059, filed Aug. 19, 2014. All of the above-referenced applications are incorporated herein by reference in their entireties.

TECHNICAL FIELD

The present disclosure relates to methods, techniques, and systems for generating a clinical activity network based on underlying application actions and database transactions in a healthcare setting.

BACKGROUND

Present day health care information systems suffer from a number of deficiencies. A core shortcoming relates to the preferred data representation model. Many prominent health care information systems represent electronic health records using a hierarchical database model, such as is provided by the MUMPS ("Massachusetts General Hospital Utility Multi-Programming System" or "Multi-User Multi-Programming System") programming language. MUMPS dates from the 1960s.

The MUMPS programming model provides a hierarchical, schema-free, key-value database. Hierarchical data models can be easy to understand and efficient to process, but can at the same time be inflexible in terms of data modeling, because they can only represent one-to-many relationships between data items.

The MUMPS hierarchical data model stands in contrast to the relational data model, first presented in 1970. (Codd, A Relational Model of Data for Large Shared Data Banks, Communications of the ACM, vol. 13:6, June, 1970.) The relational data model represents data as relations each defined as a set of n-tuples, typically organized as a table. Today, systems that use hierarchical data models have been largely displaced by relational database systems, such as those offered by Microsoft, Oracle, Sybase, IBM, Informix, in addition to various open source projects.

The market domination of relational database systems has yielded corresponding technological advances, including improved programming language support, improved management systems, better development environments, more support tools, and the like. Also, the relational database field benefits from a substantially larger community of skilled database programmers, analysts, and administrators.

Despite the advances of relational database systems, MUMPS is still widely used in some industries, including healthcare. The use of MUMPS presents the healthcare industry with a labor shortage, given the small existing community of skilled developers, system administrators and analysts. Moreover, it is difficult for healthcare organizations to implement or extend existing MUMPS-based systems, given the relatively rudimentary set of associated development environments, tools, interfaces, and the like. As a result, in many cases, healthcare organizations using MUMPS-based electronic health records cannot access their own data very easily, accurately, or efficiently.

In one stop-gap approach to addressing the problem of access to MUMPS-based data, some organizations choose to convert MUMPS-based data (e.g., health records) into relational data stored in commercial relational database systems such as those provided by ORACLE or Microsoft. Such conversion is typically performed via an Extract-Transform-Load ("ETL") process. ETL processes commonly run overnight and can take 24 hours or more before users can access the data, thereby delaying access to time-critical data. Also, many ETL processes map the incoming data to thousands of tables, resulting in a data model that is cumbersome to understand, use, or modify, even with modern tools and database management environments.

In sum, MUMPS-based electronic health records are largely inaccessible for development by modern-trained database developers, system administrators, and analysts. This inaccessibility results in reduced innovation, increased costs, poorer health outcomes, lower quality of service, and the like.

In addition, typical healthcare information systems also tend to store data in a disaggregated manner. Health records, facilities information (e.g., board and lodging information), personnel information, and accounting/billing information are typically stored in distinct databases. To make matters worse, the distinct databases may use different data formats and/or data access protocols. For example, the health records may be stored using a MUMPS-based system (as described above), while facilities information may be stored in a relational database. Each of these may use different application program interfaces, user interfaces, and the like. The disaggregation of data makes it exceedingly difficult or expensive to perform meaningful cross-sectional analyses, such as identifying implicit care processes, identifying relationships between patients and/or workers, and the like.

BRIEF DESCRIPTION OF THE DRAWINGS

FIG. 1A is a block diagram of an operational intelligence platform according to an example embodiment.

FIG. 2 illustrates elements of a clinical activity network according to an example embodiment.

FIG. 3 illustrates a clinical activity generator according to an example embodiment.

FIGS. 4A-4H illustrate example data used to generate clinical activities by an example embodiment.

FIG. 5 illustrates an example stream of updates processed by an example embodiment to generate corresponding clinical activity instances.

FIGS. 6A-6J are flow diagrams of processes performed by example embodiments.

DETAILED DESCRIPTION

Figure 1B:
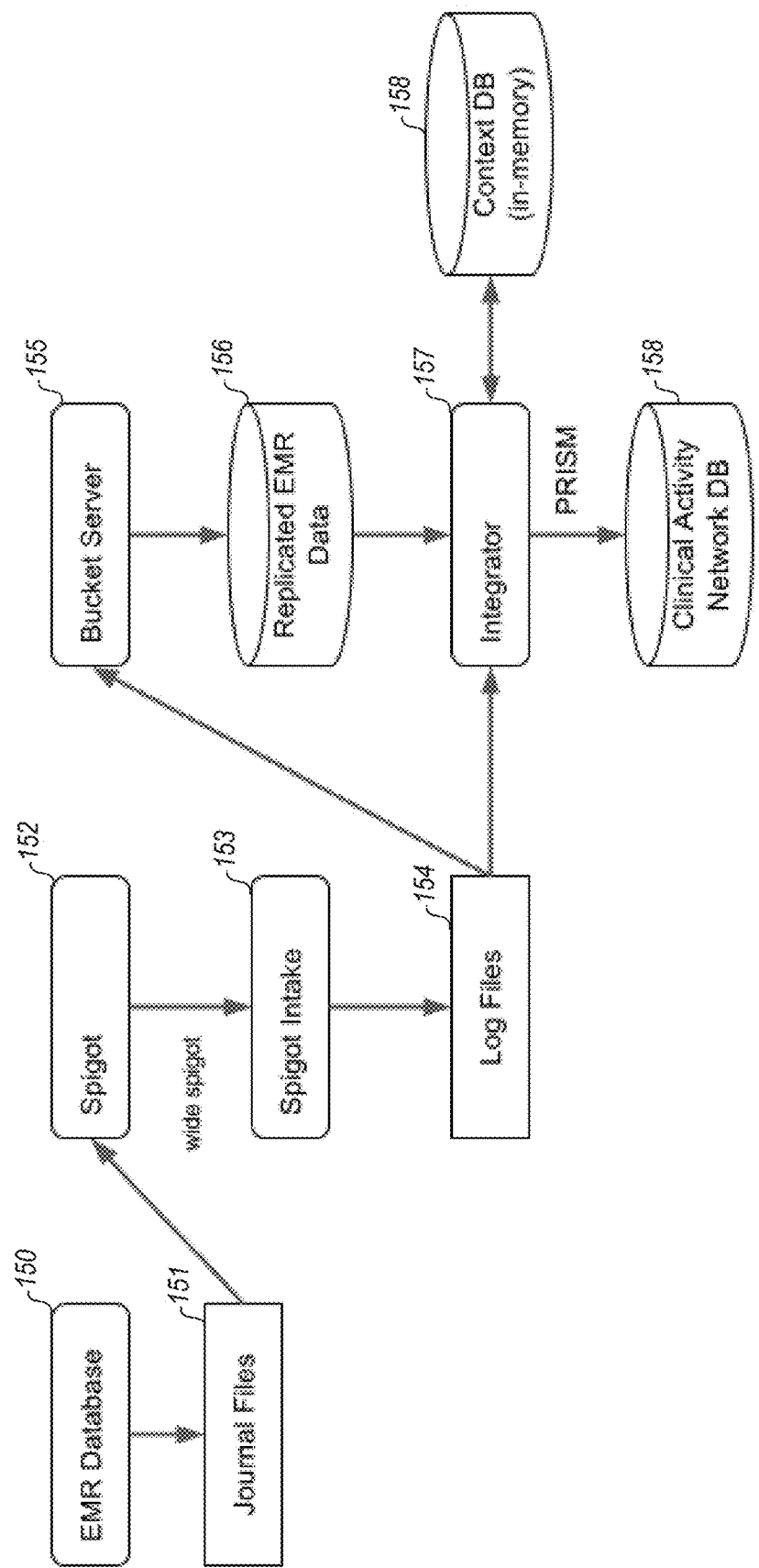
FIG. 1B is a block diagram illustrating data flows in a process for generating a clinical activity network.

Embodiments described herein provide enhanced computer- and network-based methods and systems for generating a clinical activity network from underlying application actions and database transactions in the healthcare setting. The clinical activity network may then be used to implement clinical activity network applications, including identifying relationships between persons in a healthcare setting. Some embodiments provide an Operational Intelligence Platform ("OIP") that is configured to extract and replicate electronic health records obtained from a source health care system. In some embodiments, the OIP is configured to extract electronic health record data from a source customer database that represents health records in a hierarchical format, such as a MUMPS-based representation. The OIP may also extract data that reflects the usage of computer applications within the healthcare setting. The OIP may then translate the extracted data into a relational representation.

The OIP may also facilitate the development and/or operation of client modules or applications that access (e.g., obtain, present, modify) the electronic health records in a manner that is substantially or totally independent of the source health care system. For example, a client module of the OIP may be configured to present, query, report, and generate messages related to electronic health care data that is relevant to a particular patient and that is hosted by the OIP.

The described techniques address at least some of the above-described shortcomings with MUMPS-based electronic health records. In particular, the described techniques provide a mechanism by which modern programming paradigms and technologies can be applied to data hosted by an existing MUMPS-based system, such as by providing a relational access model or a dependency-free API ("Application Program Interface") for accessing the data. Such an API facilitates access to the data via any number of modern programming languages, thereby decoupling the data from its dependencies on the MUMPS language. The OIP is in effect capable of providing real-time, relational access to existing MUMPS-based electronic health records, while respecting and retaining (at least logically) the hierarchical nature of the original electronic health records. By providing alternative models of access such as relational access, the OIP facilitates and accelerates the development of new healthcare information systems, applications, or modules, as such can be developed by the larger community of skilled developers operating technologically advanced development tools associated with the relational database market and other more modern tools/models such as Hadoop for parallel processing of large data sets and scientific-oriented "data science" languages such as R, Python and Julia.

The OIP in some embodiments facilitates real-time, dynamic, clinical analytics that deliver visibility and insight into health data, streaming events and clinical operations. The OIP may provide modules or services that allow users to run queries against streaming data feeds and event data to deliver real-time analytics and applications. The OIP may thus provide healthcare provider organizations the ability to make decisions and immediately act on these analytic insights, through manual or automated actions. In at least some embodiments, providing such functions via the OIP is based at least in part on the data extraction techniques described herein.

The OIP is also configured to generate a clinical activity network that supports the development of applications that can analyze data extracted from multiple distinct sources within a source healthcare system and/or sources external to the source healthcare system (e.g., personal health monitoring devices, health tracking systems). The clinical activity network uniformly represents operations and data updates occurring within the healthcare system by way of clinical activity instances. In some embodiments, each clinical activity instance associates an action (or activity) with a context, a time, a user, a patient or other subject, and a location if deducible. For example, one clinical activity instance may represent that a particular nurse (user) entered vitals (activity) using a patient chart form application (context) for a given patient (subject) at a particular time in a hospital/unit/bed (location). Another clinical activity instance may represent that an orderly moved a patient from one room to another. By analyzing collections (e.g., streams, groups, sets) of clinical activity instances, applications can identify patterns, processes, and relationships within the healthcare setting that would not necessarily be detectable when analyzing data from a single source, such as the source customer database.

Each of the dimensions of the clinical activity network orients the stored data with respect to a particular category, concept, or dimension. For example, in the case of a location change, the history of patient location is not necessarily captured in the medical record, but the clinical activity data will show the change in location as a transition in time. The way such transitions are typically represented are by creating timestamps in the data in the medical record. Such timestamps are arbitrarily selected by the medical record vendor provider. Embodiments of the clinical activity network will always have transitions for all data, based on its temporal order nature. All data changes have timestamps in the clinical activity network database. The clinical activity network transform all data services into temporally-ordered "databases."

Similarly, the clinical activity network transforms underlying data services and representations into a dimensionally-oriented database via the other dimensions of the clinical activity instances. For example, time is used to transform data services into a temporally-oriented database, the user dimension is used to transform data into a user-oriented database, the subject dimension is used to transform the underlying data into a subject-oriented (e.g., patient-oriented) database, and so on.

The selection and utilization of the described dimensions (i.e., time, user, subject, action, location, and context) facilitates the development of an effective operational intelligence platform. Empirically, the time, user, subject, action, location, and context fields have been observed to facilitate the representation and transformation of disorganized and disaggregated data in a manner that supports operational intelligence queries and applications. What the clinical activity network does, structurally, is turn an event stream of data, regardless of type of input (e.g., medical record, ERP, accounting, fitness device) into a logical reconstruction with key dimensions. In some embodiments, time is the strongest dimension in that all event steam instances will have a time. Not all clinical activity instances will necessarily have a user—the user may be system-generated (although system is a type of user). Not all clinical activity instances will have an identifiable subject like patient in a medical record. But there will be a subject of the event action—for example, an accounting activity for transferring assets from one balance sheet to another will have derivable or interpretable subjects. The operational intelligence techniques described herein create a structure from which essential aspects of the nature of event data are interpretable in the most generic way for the context of who, what, when, where, why questions. Such questions are not easily answered without arbitrary structures and indexes in the underlying source database.

Additional details regarding an example techniques for implementing an embodiment of an Operational Intelligence Platform are provided in U.S. Provisional Application No. 62/039,059, entitled "A DATA SYSTEM TO ENABLE HEALTHCARE OPERATIONAL INTELLIGENCE" and filed Aug. 19, 2014, the content of which is incorporated herein by reference in its entirety. Additional details regarding data extraction techniques are provided in U.S. patent application Ser. No. 14/463,542, entitled "SYSTEMS AND METHODS FOR DYNAMICALLY EXTRACTING ELECTRONIC HEALTH RECORDS" and filed Aug. 19, 2014, and U.S. patent application Ser. No. 14/693,147, entitled "SYSTEMS AND METHODS FOR DYNAMICALLY EXTRACTING ELECTRONIC HEALTH RECORDS" and filed Apr. 22, 2015, the contents of which are incorporated herein by reference in their entireties.

1. Overview of the Operational Intelligence Platform

FIG. 1A is a block diagram of an operational intelligence platform according to an example embodiment. More particularly, FIG. 1A shows an operational intelligence platform ("OIP") 100 configured to perform the techniques described herein. The OIP 100 processes (e.g., extracts, replicates, translates, analyzes) data obtained from a source healthcare system/environment 1. In this example, the source healthcare system 1 includes a customer application 2, source customer data 3, and a third-party application 4.

The customer application 2 may be, for example, a health records access and/or management application. For example, the customer application may be a form-based application used by nurses and doctors to input information about a patient's medical condition. Other types of customer applications are contemplated, including billing/accounting applications, human resources applications, scheduling applications, or the like. Some types of customer applications may be embedded in specific medical devices, such as intravenous fluid delivery monitoring applications, intensive care vital conditions monitoring applications, or the like.

In typical embodiments, the source customer data 3 represents electronic health records in a hierarchical data representation, such as may be provided by MUMPS or similar languages/data representations. In other embodiments, the source customer data 3 may be represented in other ways, such as data in a relational database. Also, the source customer data 3 may include data in addition to, or instead of, health records. For example, the source customer data 3 may include accounting data, human resource data, scheduling data, inventory data, or the like. Data 3 may include data obtained from various sources, such as application programs, sensors (e.g., from medical devices, fitness monitors), medical devices, and the like.

The third-party application 4 may be any other system, application, or device that provides data to the OIP 100, such as a personal health/fitness monitoring device or host, a weight-loss application, a social networking site, a fitness center information system, or the like. The third-party application 4 differs from the customer application 2 in that it is not necessarily under the control of the customer (e.g., the hospital or clinic) that controls or manages the customer application 2.

The illustrated operational intelligence platform 100 includes an extraction layer 101, a data manager 110, and a storage layer 111. The extraction layer 101 includes three distinct extractors 102-104 (sometimes also referred to as "spigots"). The data storage layer 111 includes a clinical activity network 112, an ontology 113, and a clinical data engine 114. While the modules of the platform 100 will be described in more detail below, the following provides an overview of their operation. The data manager 110 provides the core logic of the OIP 100. The data manager 110, in one aspect, operates as an intake subsystem, and is responsible for receiving data updates from the extraction layer 101 (including extractors 102-104), and writing them to the clinical data engine 114. The clinical data engine 114 is responsible for storing and providing access to transformed MUMPS records obtained from the source healthcare system 1.

In the illustrated embodiment, the data manager 110 is also configured to translate raw updates received from the extractors 102-104 into clinical activities that are stored in the clinical activity network 112. The clinical activity network 112 provides a uniform representation of operations performed by users of the source healthcare system 1, thereby facilitating the development of applications (e.g., client application 120) that analyze or otherwise process the clinical activity network, as described further below.

The data extraction layer 101 operates to extract data from the source healthcare system 1, the third-party application 4, and/or other data sources. The full extractor 102 is a batch or bulk extractor that is configured to extract all or a specified collection of records from the source customer database 3 or a clone, mirror, shadow copy, or backup thereof (generally referred to as "record source"). The real-time extractor 104 is configured to obtain information about data updates and/or application operations in or about real time. The real-time extractor 104 (or multiple distinct instances thereof) obtains information about events or operations performed with respect to the customer application 2 and/or the third-party application 4. Such events or operations may include user interface events (e.g., mouse clicks, button presses), application-level events/operations (e.g., open form, log in), data access events/operations (e.g., save preferences, modify record, delete file), or the like. The real-time extractor 104 can also obtain information about data updates to the source customer database 3 as they occur in or about real time. The on-demand extractor 103 pulls data records that are associated with real-time updates but that are not already present in the clinical data engine 114. For example, if the real-time extractor 104 encounters an update to a patient record that does not exist in the clinical data engine 114, the on-demand extractor 103 will obtain the required record from the source customer data 3 and store it in the clinical data engine 114, so that it can be updated as necessary by the real-time extractor 104.

The records in the source customer data 3 which are consumed by the OIP 100 may be obtained from various sources and/or represented in different ways. For example, the records may be obtained directly from the a production server/database (e.g., a live database that is serving clinicians and patients), a report shadow database (e.g., a utility copy utility copy for running reports), a production shadow database (e.g., near live, service as a backup of production), and/or a production mirror database (e.g., live, service as a disaster recovery, fail-over instance of production data). In some embodiments, the source for the records of the source customer data 3 may be specified and/or determined automatically by rule and/or conditions (e.g., to use a shadow or mirror database at certain times of day or when traffic or load on the production database increases beyond a specified level). Thus, while records are herein discussed and shown as being obtained directly from the source customer data 3, it is understood that those records may in some embodiments be obtained from sources other than a live production database of the customer. While the aforementioned is common for existing MUMPS-based databases, other data sources may have varying ways of formatting, storing, and/or representing event information such as "log files" of transactions.

Typical embodiments initially perform a full extraction of the record source, in order to populate the clinical data engine 114 with all (or a specified subset) of the records present in the source customer data 3. To perform full extraction, the platform 100 employs the full extractor 102 to process a set of records from the record source. The set of records may be all of the records in the record source or some subset thereof, as may be specified by an initial input or other configuration data. In some embodiments, the full extractor 102 obtains one record from the record source at a time. Other embodiments receive blocks of records from the record source. The full extractor 102 processes each record in no particular time order, and sends each as a message to the data manager 110. Depending on the number and size of the records in the record source, the full extractor 102 can take a significant length of time (e.g., days or weeks) to complete, depending on network speeds, size or source data, and/or other resource-related constraints. To speed up extraction and message sending throughput, multiple instances of the full extractor 102 can be run as concurrent processes or threads obtaining data from one or more record sources (e.g., production and shadow servers). In such a case, each full extractor 102 is allocated or assigned a distinct set of records to process.

During the full extraction process, real-time extraction is performed concurrently by the real-time extractor 104. To ensure that data extracted from the source customer data 3 is always current, the real-time extractor 104 is initiated before the full extractor 102. All updates to the source customer data 3 are captured by the real-time extractor 104 and thus, the extracted data, no matter how long the full extractor 102 takes to complete, will always be current. All extracted records will have been written to the source customer data 3 just prior to those records appearing in the real-time extractor 104. So long as the real-time extractor 104 is operating, an update to data in the source customer data 3 will always be reflected in the clinical data engine 114 within the operational latency (e.g., the amount of time it takes for an update to the source customer data 3 to be captured and written) of the real-time extractor 104. In some embodiments, the real-time extractor delays writing updates to the clinical data engine 114 until the full extractor has completely extracted the corresponding record.

The on-demand extractor 103 is responsible for filling in gaps in the clinical data engine 114 identified during operation of the real-time extractor 104. Given that the full extraction process can take an extended period of time to complete, and given that the real-time extractor 104 is creating and/or updating new records, there may gaps in data records stored in the clinical data engine 114. In particular, when the real-time extractor 104 initiates an update to a specified patient data record, the patient record may or may not be present in the clinical data engine 114, such as because the full extractor 102 has yet to process that record. When the record is present in the clinical data engine 114, the update to the record can be performed directly. On the other hand, when the record is absent from the clinical data engine 114, the record must be first fetched and stored by the on-demand extractor 103, so that the update can complete.

One instance of the real-time extractor 104 is responsible for capturing information about application events and/or operations performed with respect to the customer application 2 and/or the third-party application 4. Capturing application events may be accomplished in various ways. In one embodiment, the real-time extractor 104 accesses the user interface event queue of the customer application 2. In a further embodiment, the real-time extractor 104 consumes data from a journal file that tracks application-level events (e.g., user log in). In another embodiment, the real-time extractor 104 accesses a notification service provided via an API of the third-party application 4. For example, when the third-party application 4 is a personal fitness monitoring host system, the application 4 may include a publish/subscribe service that can be accessed to receive notifications regarding updates for or operations performed by a particular user.

Another instance of the real-time extractor 104 is responsible for capturing real-time updates to the source customer data 3, and forwarding those updates for storage in the clinical data engine 110. Typically, the real-time extractor 104 is run as a process or similar unit of computation (e.g., thread) on a system that hosts the source customer data 3. For example, the real-time extractor 104 may be run as a process on a server that hosts a production, shadow, or mirror database that stores the source customer data 3.

In one embodiment, the real-time extractor 104 taps into data as it streams into one or more journals associated with the source customer data 3. As customer application 2 writes data to the source customer data 3, the data is first stored in a journal file. The real-time extractor 104 copies data written to the journal file, converts it into a message, and forwards the message to the data manager 110, for storage in the clinical data engine 114.

Journal files, or "log" files, are files that are created in the source healthcare system 1 by the database management system hosting the source customer data 3. For example, a MUMPS database creates (or updates) journal files as its database is updated or otherwise modified. In some embodiments, each change to the database is written to the database and to a journal file. Journal files are typically created in chunks (e.g., 1 GB of data at a time) and written to disk using a sequential ordering scheme together with the implicit timestamp of the last write. Journal files that are processed the real-time extractor 104 are typically processed in time-based order, from oldest to newest. In some embodiments, a real-time journal reader operating as part of the extractor 104 reads data as it is being written, not after the file (chunk) completes.

The data manager 110 provides the core logic of the OIP 100. For example, in one aspect, the data manager 110 functions as an intake subsystem, and is responsible for receiving data updates from the extractors 102-104, and writing them to the clinical data engine 114. The data manager 110 receives messages from the extractors 102-104. The received messages include data from the source customer data 3. In response to the received messages, the data manager 110 determines whether and what types of additional processing or translation is required, and then performs a corresponding storage operation in the clinical data engine 114.

The illustrated data manager 110 includes a clinical activity generator 116. The generator 116 translates the messages received from the extractors 102-104 in order to generate clinical activity instances, which are stored in the clinical activity network 112. A clinical activity instance is a logical representation of an activity performed within a clinical setting. A clinical activity instance may be generated based on a data update to source customer data 3 and/or an operation (e.g., user interface event) performed with respect to the customer application 2. In a typical embodiment, each clinical activity instance associates a context (e.g., an application) with an operation/activity/action (e.g., open patient form), a time, a user (e.g., the operator of the application), and a subject (e.g., the patient).

The clinical data engine 114 includes data extracted or replicated from the source customer data 3. The clinical data engine 114 may be a scalable, highly available database that is used to store the data obtained by the extractors. Typically, the clinical data engine 114 substantially replicates the contents of the source customer data 3, but does so in a different and/or more efficient representation. In some embodiments, the clinical data engine 114 stores data using a Log Structured Merge Tree format. The LSM format is a tree-based format that can efficiently represent sparse key-value data, such as is common in the health records context, especially those the use b-tree like data representations. In addition the LSM format allows for the storage of data contiguously on disk, making it ideal for recollecting data about a given data topic, such as Patient medications history. Example LSM-based storage systems include RocksDB, LevelDB, or the like.

Furthermore, the clinical data engine 114 and/or other aspects of the platform 100 provide access to the source customer data 3 in a manner that decouples the data from a specific implementation or management language (e.g., MUMPS). For example, the clinical data engine 114 may provide access to multiple different programming technologies via a Web-based API, SQL-based database drivers, and the like.

The ontology 113 is an ontology database that represents the concepts of the particular deployment, such as the types of activities, actions, users, and contexts that can occur in the healthcare setting. The ontology represents activities and other concepts that cannot or are not directly represented in the underlying source customer data 3 or clinical data engine 114. For example, when a nurse uses customer application 2 to enter information about a patient's vital signs, the source customer data 3 may reflect the fact that an entry to a patient record has been made, but may not reflect that this entry relates to a check of the patient's vital signs, that this entry was made with a particular application, that this entry was made by a particular user, or the like. The ontology 113, however, represents the user, the application, and the action ("enter vitals"), in a manner that can be used to generate a clinical activity that is stored in the clinical activity network 112, as described below.

The clinical activity network 112 is a semantic network that represents the activities that are themselves represented by data items stored in the clinical data engine 114 and/or the source customer data. For example, the semantic network may represent an activity such as a patient bed change that is represented by two distinct updates to a patient record. As another example, the semantic network may represent an activity such as a drug administration, which is represented by multiple distinct updates to the patient record (e.g., a drug prescription entry, a drug acquisition entry, a drug administration entry). The semantic network typically also associates activities with time, thereby imposing a time ordering on activities, something which is not present in source customer data itself, because the source customer data typically provides only a "present time" snapshot of the state of a patient record and related data. By using these techniques, the system can represent, track, and analyze logical activities that map to one or more actual clinical actions and events that are represented in the source customer data, even though the source customer data does not by itself represent the activity and rather only represents the ground-level facts as data updates to a patient record.

The ontology 113 addresses some of the shortcomings of the prior art by adding a layer of meaning to raw data produced by a variety of data sources within the source healthcare environment or system. The ontology 113 facilitates the generation of the clinical activity network 112 by associating or mapping raw events obtained from the source healthcare system to meaningful clinical activity instances stored in the clinical activity network 112. In at least some embodiments, the ontology 113 is not a static representation meaning within a given source environment. Rather, the ontology 113 is developed and modified over time as new client applications 120 are developed and deployed. When a new client application 120 is developed, raw events from the source healthcare system are analyzed and given meaning within the ontology 113, such as by associating a raw event (or sequence or pattern thereof) with an ontology object, which is or includes a token, symbol, data structure, or other semantic indicator within the ontology 113. In this way, the ontology 113 facilitates reuse of previously defined ontology objects, thereby increasing in explanatory and developmental power over time. In some cases, raw events are associated with ontology objects (e.g., that are stored in the ontology 113) that provide one or more of: a human-readable description of the activity, a machine-readable identifier (e.g., that uniquely identifies the type or class of activity), one or more methods or functions that can be performed on or with the object, rules and/or functions for performing inbound/outbound translations of raw events to clinical activity instances, one or more links to related ontology objects (e.g., superclass or super type links for representation of hierarchy of ontology objects), or the like.

The data manager 110 also includes a notifier 118. The notifier 118 may provide to a client application 120 real-time information about activities, events, and other operations occurring within the source healthcare system 1. For example, the notifier 118 may notify the client application 120 of clinical activity instances as they are generated by the generator 116. The operation of the notifier may be configured by the client application 120 in order to filter activity instances, such as to only provide notifications related to a specified user, patient, action, context, time, or combination thereof. The notifier 118 may communicate with the client application 120 via a publish/subscribe mechanism, API calls, or the like.

Although the techniques are primarily described in the context of healthcare systems, the techniques are equally applicable to other business contexts, such as banking, inventory systems, customer relationship management systems, human resources systems, or the like.

Note also that although the platform 100 is described as having a specific set of modules, other embodiments may decompose the functionality of the platform 100 in other ways. For example, rather than using a distinct on-demand extractor 103, another embodiment may integrate the functions of the on-demand extractor 103 into the real-time extractor 104. Also, while the data of the platform 100 is shown as decomposed into three distinct units 112, 113, and 114, embodiments may actually use any number of data stores (e.g., databases), including a single one, to store the three data collections.

FIG. 1B is a block diagram illustrating data flows in a process for generating a clinical activity network. The modules and data illustrated in FIG. 1B are examples from a specific implementation of one embodiment of an operational intelligence platform 100.

As shown in FIG. 1B, updates to an electronic medical records database 150 are reflected in journal files 151. The medical records database 150 is an example of source customer data 3. The database 150 is typically updated by an application, such as a patient chart application or the like. The updates thus reflect events or operations that occur within the clinical setting. The journal files 151 are used by the database 150 to record updates, deletes, and other transactions in a persistent manner.

A spigot process 152 consumes updates from the journal files 151. In this implementation, the spigot process 152 processes the updates to convert them into a standard format, and forwards the processed updates to a spigot intake 153. The spigot process 152 and spigot intake 153 are elements of the data extraction layer 101 discussed with respect to FIG. 1A, above. In some implementations, the spigot process 152 may execute on the same system (e.g., the same computer or cluster of computers) that executes the EMR database 150. That is, the spigot process 152 may execute on a system that is controlled by the hospital or other entity that controls or otherwise manages the source healthcare system 1.

The spigot intake 153 receives updates in a standardized format and stores them in log files 154. By storing updates in log files 154, the spigot intake 153 can efficiently record updates at very high throughput, limited only by the throughput of the underlying file system.

Updates stored in the log files 154 are consumed in this implementation by two distinct processes: a bucket server 155 and an integrator 157. The bucket server 155 functions to consume and store updates from the log files 154 into a replicated EMR database 156. The database 156 is an example of the clinical data engine 114 of FIG. 1A.

The integrator 157 is an example of the generator 116 discussed with respect to FIG. 1A. The integrator 157 in this example consumes information about events (in the form of updates stored in the log files 154 and/or the replicated database 156) and generates activity instances that are stored in a clinical activity network database 158.

When generating activity instances, the integrator 157 also stores and references state information stored in a memory-resident context database 158. The context database 158 is an example of an ontology 113, as it includes information that guides, informs, or controls the generation of clinical activity instances. The state information stored in the database 158 may include information related to user/subject identity, location, partially completed activities, activity analysis windows, activity generation patterns or rules, or the like. As will be discussed further below, in some cases an activity instance may be based on multiple underlying updates/events received from the source system. For example, an activity such as "update vitals," may be based on three separate updates, one each updating blood pressure, temperature, and heart rate. Thus, the integrator 157 may generate (e.g., upon encountering an initial update to blood pressure) an analysis window that is used to collect, coalesce, or otherwise track events until a sufficient amount of information has been received to generate a fully formed activity instance. As another example, the integrator 157 may learn of a patient's location (e.g., room number) based on a room assignment update, an equipment order, a cleaning order, or other event. This location may also be stored (in association with an identifier of the patient) in the context database 158 so that it can be referenced and/or utilized during the generation of subsequent activity instances.

2. Clinical Activity Network

FIG. 2 illustrates elements of a clinical activity network according to an example embodiment. In particular, FIG. 2 depicts a graph 200 that includes an activity context 201, an action 202, a user 203, a patient 204, and a time 205. Optionally, other dimensions (e.g., location) 206 may be represented. Together, the items 201-206 can be used to represent a clinical activity. The items 201-206 can be represented as various ways such as nodes in a graph, references in a tuple, columns in a database, or the like. The following provides an overview of the elements of a clinical activity. The generation of clinical activities based on underlying application or data-specific operation operations or actions is described further below, with respect to FIGS. 3 and 4A-4H.

The activity context 201 represents the specific context where a given activity occurs. Typically, the activity context is represented via an identifier that is defined in the ontology database 113. The represented activity context generally represents a logical unit that aggregates or groups actions and/or data. The context may be a category, feature, property, or facet of the customer environment, such as patient vitals, history, or account in the healthcare setting. The represented activity context can also or instead be (or be related to) a form, menu, window, or the like displayed by a customer application. The customer application may be a native application executed directly via an operating system, a browser-based application, or the like. In most cases, the activity context 201 provides context for an action 202. The activity context 201 provides a mechanism for aggregating actions 202. Thus, multiple distinct actions may be linked by or contained within a single activity context 201.

Some embodiments organize contexts as a classification or semantic hierarchy or graph. In the healthcare context, a classification hierarchy may have a root context of "Health." The root context may have sub-contexts (e.g., Patient, Nurse, Doctor), which may each have one or more sub-contexts. For example, the Patient context may have patient chart, patient history, and patient accounting as sub-contexts. In a hierarchy-based embodiment, the context may be a reference to a particular context stored in the hierarchy or to a context "path," which represents the chain of contexts from the root to the specified sub-context.

The action 202 represents a specific action within an activity context. The action 202 represents the data or state of a given event or activity occurring in the activity context. The action 202 is typically based on one or more application actions, such as opening a form, entering a data item, deleting a data item, or the like. The action 202 may also or instead be based on one or more user interface events, such as a button click, a menu selection, data entry, or the like. In other cases, the action 202 may represent data access operation, such as a file access (e.g., open, close, read, write), a database operation, or the like. The action is typically represented via an identifier that is defined in the ontology database 113.

The user 203 represents the user associated with the activity. Typically, the user is the person performing the modeled activity via an application, database, or other customer system module. The user 203 is represented by an identifier stored in the clinical data engine 114. The OIP 100 tracks users via login identifiers (e.g., user names) and/or process identifiers that are managed via the source healthcare system 1. In addition, the user 203 may have associated properties, such as environment settings, roles (e.g., nurse, physician), and the like.

In some cases, the OIP 100 translates identifiers managed by the source healthcare system into user identifiers managed by the OIP 100. For example, when the OIP 100 is notified of a particular activity taking place with respect to a customer application 2, the OIP 100 may receive a process identifier used by the operating system that hosts the customer application 2. The OIP 100 may then reference a mapping between process identifiers and user identifiers to determine the identity of the user who is operating the customer application 2. In some embodiments, the OIP 100 may manage this mapping, such as by tracking log in/logout events which can be used to associate user identifiers with process identifiers. In other cases, the OIP 100 may determine a user identifier by reference to a customer database that associates user identifiers with process identifiers of database connections corresponding to an applications operated by users.

The patient 204 represents the subject of the activity, typically a patient that is associated with the activity. Other types of subjects may be represented in other contexts, such as client (e.g., in a law firm setting), guest (e.g., in a hospitality context), or the like. The patient 204 may be represented by an identifier stored in the clinical data engine 114. In some cases, the patient may also be the user 203 associated with the activity. For example, if the patient (or other subject) performs an operation with a personal health tracking device, the patient will be both the patient 204 and the user 203.

The time 205 is the wall clock time (or time range) at or about the time at which the modeled activity is identified by the OIP 100. Other time points may also or instead be measured, such as the time that the OIP 100 receives a notification of the underlying action (e.g., menu operation), which typically occurs shortly before the formal identification and generation of the activity by the OIP 100. In some cases, the source customer system may associate multiple distinct times with a given event. For example, a journal file may represent a time at which an update was stored in the journal file (a "journal timestamp") and a time provided by the application which initiated the data update operation (an "application time"). In some cases, the journal timestamp associated with an update not a reliable indicator of the time at which the event giving rise to the update actually occurred. For example, the source customer system may associate the same journal timestamp with a large number of updates, even though those updates were all received or initiated at different times. In such cases, time may be represented by the OIP 100 as a time range in order to account for uncertainty with respect the actual event time. The ranges may be narrowed, tightened or otherwise bounded by other sources of time, such as application times that appear at certain points in the journal and that are known to be more reliable than journal timestamps.

The other dimension 206 represents the optional inclusion of another category or dimension, such as location. For example, some embodiments may in addition include a location, such as one or more identifiers that represent the physical geographic location of the activity, such as hospital, division, clinic, floor, room, GPS location, or the like. Location may be determined in a variety of ways, such as via machine-readable indicia (e.g., active or passive RFID systems), smart mobile devices (e.g., smart phones with tracking/beacon apps), network location (e.g., from Wi-Fi routers), or the like.

Other embodiments may utilize a greater or lesser number of dimensions when representing a clinical activity. For example, an activity may also or instead include a link field, which can be used to tie or otherwise associate the activity to or with one or more other activities. While the particular dimensions utilized in the examples herein have been shown to facilitate the development of an effective operational intelligence platform, the techniques described herein may in some embodiments be performed with a greater or lesser number of dimensions and/or different types of dimensions.

3. Generating Clinical Activity Instances

FIG. 3 illustrates a clinical activity generator according to an example embodiment.

In particular, FIG. 3 depicts a clinical activity generator 116 that is configured to identify clinical activities based on actions or operations occurring with respect to underlying application actions and database transactions in a healthcare setting. The following provides an overview of the inbound and outbound data flows of the process of generating clinical activities. Examples of the generation of clinical activities are provided with respect to FIGS. 4A-4H, below.

The clinical activity generator 116 converts information about underlying system events, such as application actions, database operations, system notifications, and the like, into clinical activities that are stored in the clinical activity network database 112. In this example, the clinical activity generator 116 converts information provided by multiple data streams 301a-301d. The data streams 301a-301d may be provided by modules of the data extraction layer 101, such as the real-time extractor 104 described with respect to FIG. 1A.

Each stream 301a-301d is a stream of data provided by or obtained from an underlying application, process, database or the like. For example, source customer application stream 301a is a stream of data about application events, user interface events and/or other operations occurring with respect to, for example, the source customer application 2 of FIG. 1A. Source customer database stream 301b is a stream of data about database updates and other operations performed with respect to, for example, the source customer database 3 of FIG. 1A. Personal fitness monitor stream 301c is a stream of data about events and operations occurring with respect to a personal fitness or health monitoring device. Other types of streams are contemplated, as represented by stream 301d.

The data in each stream 301a-301d can be obtained in various ways. For example, the application stream 301a includes data about application events that may be obtained by accessing the event queue of the operating system that hosts the underlying source customer application. The database stream 301b includes indications of database operations that may be obtained by accessing a journal file used by the database 3 of FIG. 1A. In other embodiments, information about database operation may be obtained based on events provided by the database, access to a database driver or API, or the like. The fitness monitor stream 301c may include data that is obtained based on notifications provided by fitness or health monitoring device. Alternatively, or in addition, the data in the stream 301c may be obtained from a computing system, possibly distinct from the monitoring device itself, which manages or stores the health information collected by the monitoring device.

Each stream 301a-301d provides data to a corresponding parser 302a-302d. As will be described further below, the parsers 302a-302d are responsible for converting data obtained from a stream into a data structure (e.g., pattern, parse tree, template) that can be converted by the clinical activity generator 116 into a clinical activity for storage in the clinical activity network 112. In typical embodiments, the information received by a parser from a stream 301a-301d is in a textual format. The parser is configured to read the textual representation of events, operations, or actions, and form a pattern or similar structure that is passed along to the clinical activity generator 116. Each stream may provide data in a different format. Thus, the parsers 302a-302d may be customized or specialized to operate on streams from specific types of applications, systems, databases, or devices.

The parsers 302a-302d provide parsed data to the clinical activity generator 116. The parsed data is in some embodiments a pattern or other parse data structure that is used by the identifier 300 to generate a corresponding clinical activity. The clinical activity generator 116 may reference the ontology database 113 and/or the clinical data engine 114 based on the parsed data. For example, the parsed data may include one or more identifiers of an application event (e.g., "Open" and "PatientForm"). The parse data may also include information about or related to the user and the patient, such as process identifiers, user identifiers, patient identifiers, and the like. These identifiers may be mapped, via the database 113 or 114, to a corresponding activity context, action, user, and patient. The activity context, action, user, and patient, together with receipt time, can then be aggregated by the generator 116 to generate a clinical activity event. The generated clinical activity event is then stored in the clinical activity network database 112.

FIGS. 4A-4H illustrate example data used to generate clinical activities by an example embodiment. In particular, FIGS. 4A-4H are data tables that include example information about applications or database operations and the corresponding clinical activities that are generated therefrom using the techniques described herein.

FIG. 4A depicts a table 400 that describes example activities and contexts. For example, the first row of table 400 describes a PatientChart context, which arises when a user performs the operation of moving to or opening a patient chart form within a healthcare application. When the user performs this operation, text data such as "PatientChart (Z59777)" is recorded in the customer database 3.

The OIP 100 learns of this operation through the actions of the real-time extractor 104 or a similar component that is monitoring the customer database 3 and/or the customer application 2. The processing performed by the OIP 100 can be expressed as follows:

| Input: | "PatientChart(Z59777)" |
|---|---|
| Pattern Match: | "PatientChart(" + PatientIdentifier + ")" |
| Output: | 1) AC2501 (the unique ID in the Ontology DB) |
| | 2) SubjectTypeID 1 |
| | 3) Subject Z59777 |

In the above, the input is the text string that is parsed by the parser 302b. The pattern match is the output of the parser 302b, which is passed to the activity generator 116. The activity generator determines the activity identifier (AC2501), the subject type identifier, and the subject identifier by reference to the ontology database 113 and/or the clinical data engine 114.

The activity generator 116 then creates a fully formed activity instance, which can be expressed as follows. In this example, the activity instance is represented in JavaScript Object Notation (JSON) format, but other formats (e.g., XML) are contemplated:

```
Generated Activity Instance:
ActivityInstance {
    {"UserID",        "MSHN101"              },
    {"Activity",      "PatientChart(Z59777)" },
```
```
    {"FeedID",        "FT01"                 },
    {"ReceiptTime",   "08/02/14 @ 3:27:14am" },
    {"ActivityID",    "AC2501"               },
    {"SubjectTypeID,  "1"                    },
    {"Subject",       "Z59777"               }}
```

As another example, the second row of table 400 describes an Enter Vitals activity, which arises when a user performs the operation of entering data into the patient chart form of the healthcare application. In particular, the user (e.g., nurse) enters pulse, blood pressure, and breathing into the patient chart. In this case, the OIP 100 receives the string "EV.PatientChart(Z59777, 99, 129/89, 22)," which is parsed to identify the PatientChart context, the Enter Vitals activity (based on the field EV), and the associated patient identifier Z59777. Given this information, the activity generator 116 creates and stores a corresponding clinical activity instance in the clinical activity network database 112.

The processing performed by the OIP 100 with respect to the second row of the table 400 can be expressed as follows:

| Input: | "EV.PatientChart(Z59777,99,129/89, 22)" |
|---|---|
| Pattern Match: | "EV" + "." + "PatientChart(" + PatientIdentifier + text + "," + numeric text + ")" |
| Output: | 1) AA902 |
| | 2) SubjectTypeID 1 |
| | 3) Subject Z59777 |

```
Generated Activity Instance:
ActivityInstance {
    {"UserID",        "MSHN101"                              },
    {"Activity",      "EV.PatientChart(Z59777,99,129/89, 22)"},
    {"FeedID",        "FT01"                                 },
    {"ReceiptTime",   "08/02/14 @ 3:27:14am"                 },
    {"ActivityID",    "AA902"                                },
    {"SubjectTypeID,  "1"                                    },
    {"Subject",       "Z59777"                               }}
```

Note that there are various ways to interpret the input pattern specification. The patterns can be M (the MUMPS programming language) routines or functions from any programming language. It the table of FIG. 4A (and the others in this sequence) the illustrated pattern is a pseudo-language for specifying input data that is used to infer or otherwise identify a node in the clinical activity network.

FIG. 4B depicts a table 410 that represents the activity instances as stored in the clinical activity network database 112. Ellipsis in table 410 represent rows not shown in the example for clarity. Note that each activity is associated with a unique identifier (CAN ID). Each activity also references data items that are represented in other databases. For example, the User ID and Subject ID fields contain a references to persons that are represented in the clinical data engine 114. The Activity ID field contains a reference to an activity represented in the ontology database 113.

FIG. 4C depicts a table 420 that represents a simplified view of the table 410 of FIG. 4B. Table 420 differs from table 410 in that table 420 does not include a Subject column. Each activity has a subject that is typically a person, such as a patient, client, or employee. Note that the subject need not be a natural person. For example, the activity subject may be an organizational entity (e.g., corporation, business unit, employee group), a production or supply chain element (e.g., production or transportation unit, production input), or the like. In this example, and the ones that follow, the Subject field is implied as being a patient subject.

FIG. 4D depicts a table 430 that represents example activities stored in an ontology database. The table 430 includes both activities that are related to a patient's medical record, such as activity AA902 (enter vitals) and AA877 (enter a note). The table 430 also includes activities that are not directly related to a patient's medical record, such as activities AA310, which represents the operation of entering a bed location for a patient.

By representing activities that are related to different facets of patient care, such as medical care, room and board, and the like, the OIP can identify and analyze processes and transitions occurring within a healthcare setting. Because the OIP represents activities in a uniform manner, the OIP can perform cross-sectional analysis that is difficult or impossible to perform using traditional approaches, which may be limited to analyzing data that is segregated into distinct silos, for example, in a first database that contains medical information, a second database contains room and board information, and a third database that include insurance and payment information.

FIG. 4E depicts a table 440 that represents example clinical activity instances related to an example patient care scenario. In this scenario, Nurse Bob, MSHN122, places the patient in Bed BA10. The next day, Nurse Sue, MSHN101, places the patient in Bed BC12. The transition of a patient moving from one bed to another is captured through from the stream into the OIP:

08/02/14 @ 9:44:14 pm, MSHN122, Z59777, EnterBed.FTBoard(Z59777,BA10)

Followed later the next day by . . .

08/03/14 @ 5:31:34 pm, MSHN101, Z59777, EnterBed.FTBoard(Z59777,BC12).

Given the above events, the processing performed by the OIP can be expressed as follows. Note: SubjectTypeID is simplified and not in the output

| Input: | "EnterBed.FTBoard (Z59777, BA10)" |
|---|---|
| Pattern Match: | "EnterBed" + "." + "FTBoard(" + PatientID + numeric text + ")" |
| Output: | 1) AA310 |
|  | 2) Patient Z59777 |
| Input: | "EnterBed.FTBoard (Z59777,BC12)" |
| Pattern Match: | "EnterBed" + "." + "FTBoard(" + PatientID + numeric text + ")" |
| Output: | 1) AA310 |
|  | 2) Patient Z59777 |

The outputs above are represented by CAN IDs 13299 and 13385 in table 440. The fact that room and board related activities are uniformly represented together with medical chart related activities enables cross-sectional analysis. For example, correlations between patient health and room location can be discovered.

FIG. 4F depicts a table 450 that illustrates the use of different types of data feeds. In general, there is no limits to the number and types of data feeds. For example, information about the vital signs (e.g., blood pressure) may be obtained from a fitness or health monitoring device worn by a patient, even when that patient is not in a hospital or other in-patient facility. Such an activity can be represented as CAN ID 14088 in table 450. Note in this example that the User and the Patient field reference the same person.

FIG. 4G depicts a table 460 that represents an undefined activity. In some cases, the OIP is notified of activities that are not represented in the ontology database. Such undefined activities can be identified when the parsed input pattern does not match against any activity stored in the ontology database 113. Undefined activities may occur for various reasons, such as because the ontology database 113 has not yet been fully implemented to represent every operation that can occur in a given setting, because a new feature is added to a healthcare application, because a new type of data element is being stored in a healthcare database, and the like.

The processing performed by the OIP with respect to undefined activities can be expressed as follows:

| Input: | "SLevel. FTBoard(Z59777,10)" |
|---|---|
| Pattern Match: | "SLevel" + "." + "FTBoard(" + PatientID + numeric text + ")" |
| Output: | 1) UNDEFINED for |
|  | 2) Patient Z59777 |

Note that in this case, the input text was successfully parsed. However, the SLevel field could not be matched against any activity represented in the ontology database. Table 460 records the above activity as CAN ID 13289. Note that although the SLevel could not be matched, other fields of the activity have been determined, including the User ID, Subject, and context (FTBoard).

Recording undefined activities facilitates a number of important operations. For example, the OIP may provide reports or other information regarding undefined activities (e.g., a list of undefined activities observed during a specified time period), so that such activities can be analyzed (by human or machine) in order to extend and/or revise the activity ontology. For example, it may be determined that the SLevel activity refers to the entry of a strength level, on a rating of 1 to 10. Once an undefined activity is defined in the ontology, the OIP may backfill corresponding activity instances in the clinical activity network database, by modifying the corresponding instances to reflect the newly determined definition, such as by changing the Activity ID field from UNKNOWN to a concrete activity identifier in the ontology database.

In some cases, such as when the syntax or format of the input text is extended or otherwise modified, the parser may fail to parse the text and produce a pattern. Unparseable inputs may be handled in a manner similar to that used for undefined activities. In particular, the input text is stored in the clinical activity database with an identifier that indicates that the input text could not be successfully parsed. In response to such an entry, the OIP may notify an administrator or other party, so that the corresponding parser may be updated. Unparseable entries may then be backfilled, by reparsing the stored input text.

FIG. 4H depicts a table 470 that represents aspects of a protocol used by the OIP for communicating and processing information about clinical activities. The described elements may be represented as fields in a database, components of a data structure, fields of a messaging format, or the like.

FIG. 5 illustrates an example stream of updates processed by an example embodiment to generate corresponding clinical activity instances. FIG. 5 depicts a table 500 that represents six successive updates to a source customer database 3. In this example, the source customer data is represented in key-value format, where each row of the table 500 represents a new value to be stored with respect to a given key. The values are in text format and are pipe ("|") delimited.

For each key, the variable name indicates the schema of the subscripts in parentheses. For example, in row 1, the variable name is ENU, which has the following subscripts (INI, ID, ITEM, LINE). The key is parsed or otherwise decomposed into constituent parts that are used to identify the type of operation being performed. In this case, the combination of INI=FSD and ITEM=1000 in row 1 identifies this row as a flowsheet entry. A flowsheet is a type of patient record that is used to track the condition of a patient (e.g., pulse, temperature, weight) and/or interventions performed (e.g., medicines administered).

Once the generator 116 has determined that the data item in row 1 corresponds to a flowsheet entry, the following flowsheet-specific procedure is used to construct a clinical activity instance including the following dimensions: subject, user, timestamp, action context, action item.

In this example, the subject for a flowsheet entry is the patient. The patient ID is part of the flowsheet record and can be retrieved from the retrieved from the clinical data engine 114 (which includes replicated medical records) by using the ID subscript in sample row 1 (99500000).

The user for this example flowsheet entry is the caregiver making the observation. Their user ID is part of the flowsheet entry value (item 4), which is RJT1 in the sample row 2. Note that in some cases the user ID may not be part of the flowsheet entry, and is obtained by an indirect mechanism, described further below.

The time for this example flowsheet entry is the time the measurement was made.

This is also part of the flowsheet entry value (item 2), which is 5477659371[PDT in the sample row 2. Note that there are two times in row 2. The first time corresponds to the time of the observation, and the second time corresponds to the time the entry was made. In other cases, only a single time or other times may be represented and/or used.

The location for this example flowsheet entry is the location of the patient. There are several different types of locations, such as a bed in a hospital, a provider's office, the home, or the like. Location information for a patient can be determined various ways. In some cases, the location is indicated by previously encountered data in the stream, and stored in the context database (FIG. 1B). The subject ID can be used to query the context database for the patient's location a given time.

The action context for this example flowsheet measure includes an encounter ID, account ID, and flowsheet template used. The encounter ID and account ID are found by making appropriate queries to the replicated records in the clinical data engine 114 using the flowsheet ID subscript in sample row 1 (99500000). The template used is part of the flowsheet entry value (item 20), which is empty in sample row 1.

The action item for this example flowsheet entry includes the actual measurement data. This includes the measure ID and the value, which are part of the flowsheet entry values. The measure ID is item 1 and the value is item 6 is rows 2 and 6. In the case of flowsheets, many measurements may be taken as a group which come through the stream as separately interleaved with other unrelated data. In the sample stream data, row 6 contains another flowsheet entry with the same flowsheet ID, user and timestamp. When row 1 is encountered a forward through the data window is performed to collect together all these flowsheet entries to create a single action item. In the example, the measure IDs and values from rows 1 and 6 are combined to construct the action item [(6,98.20004), (2204,116)].

Note that in this case, the generator 116 analyzes multiple data items (updates) to generate a single clinical activity instance. Some of the updates are not relevant to the specific instance being generated in this example (e.g., rows 3 and 4), while other updates include data items that are coalesced into a single clinical activity instance (e.g., rows 1, 2, 5, and 6).

The data shown in table 500 can be represented in other ways. In some embodiments, the extraction layer performs some processing on received events, such as to translate events into a standardized format. One embodiment translates (e.g., by the extraction layer) all received events into a "wide" format described in Table 1, below. In this format, each event is translated into a standard, newline-terminated format record having the fields described below.

TABLE 1

| Field Name | Description/Contents |
| --- | --- |
| hostname_length | 2-byte length of hostname |
| hostname | IP address, host name, or other identifier for system providing the source event. Hostname is sent for the first journal entry for every journal file. For remaining entries host name is not sent. |
| filename_length | 2-byte length of journal filename |
| filename | Journal file name. Journal name is sent for the first journal entry for every journal file. For remaining entries journal name is not sent. |
| op_type | 1-byte identifying the type of operation. Value of 255 (−1) is sent for "end of journal" record with previous address as the last address sent and current address as 0. Only Set and Kill operations are sent by the protocol. |
| process_id_length | 1-byte length of process identifier |
| process_id | Identifier of process providing the source event. Note that process ID is used here instead of user ID. Other embodiments may use user ID instead or in addition to process ID. Also, some embodiments can determine a user ID based on a given process ID, as discussed below. |
| previous_address | 4-byte previous address field |
| date and time | 8-byte number denoting date and time, in some embodiments measured in milliseconds since Jan. 1, 1970 |
| reference length | 2-byte number denoting length of global reference field |
| global reference | Global reference plus subscripts (e.g., column 2 in FIG. 5) |
| value length | 4-byte number denoting length of the value field |
| value | New value for the global (e.g., column 3 in FIG. 5) |
| newline | ASCII character 10 |

As noted above, in some circumstances a user ID not be part of a source event. For example, the source event may instead use an identifier of the process that gave rise to the event. In such cases, the generator or other module of the Operational Intelligence Platform identifies the user with reference to other data, including other event streams, operating system associations, or the like. In one embodiment, the source healthcare system stores in a separate journal file events that correspond to user log in and log out events. Such an event associates a process ID with a user ID, along with possibly other information, such as time, workstation identifier, or the like. This association is tracked and stored by the OIP. Then, when a source event is encountered that uses a process ID (as opposed to a user ID), the OIP determines the user ID by looking up the process ID and finding the corresponding user ID. The OIP tracks the log in and log out events in substantially real time, so that the association between process IDs and user IDs is always up to date with respect to the actual activities of users on the source healthcare system.

3. Example Processes

FIGS. 6A-6J are flow diagrams of processes performed by example embodiments.

Figure 6A:
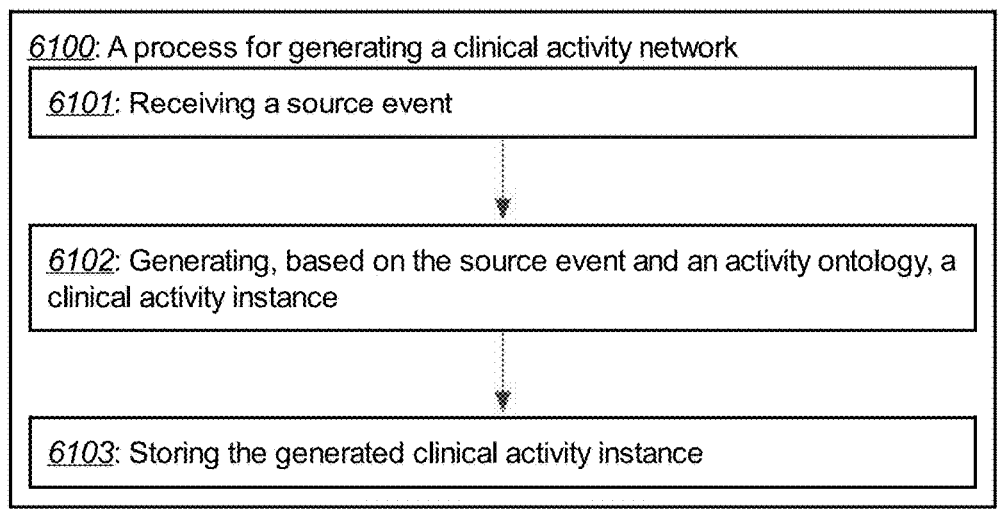

FIG. 6A is a flow diagram of example logic for generating a clinical activity network. More particularly, FIG. 6A illustrates a process 6100 that includes the following block(s).

Block 6101 includes receiving a source event that represents a database update event or an application event caused by an activity performed in a source healthcare system. Receiving the source event may include receiving from one of the extractors 102-104 text data that represents an application event or database update event caused by an application or other process executing within the source healthcare system 1. Note that the activity may be human-generated or caused, (e.g., by human interaction with an application) or caused by some autonomous program or device (e.g., a fitness monitoring device, an intensive care patient monitor). Also, the term "source healthcare system" is to be broadly construed, such as to include traditional health-records related systems at hospitals or clinics, but also related systems found in those settings (e.g., accounting systems, human resource systems, inventory management systems), in addition to systems or devices found outside of the traditional healthcare setting, such as home monitoring systems, personal fitness monitors, and the like. In some embodiments, at least some of the clinical activity network is generated in or about real time. For example, the process may receive data from the real-time extractor 104, which provides updates regarding database update operations and/or customer application operations. The received data is dynamically transformed into clinical activity instances for storage in the clinical activity network database 112, as described further below.

Block 6102 includes generating, based on the source event and an activity ontology, a clinical activity instance that identifies a context, an action, a user, and a subject. The process next generates a clinical activity instance that corresponds to or is otherwise associated with the source event. Generating the clinical activity instance is also based on an ontology, which is a structure or representation of knowledge about the underlying source healthcare environment. The ontology informs, controls, and/or directs the generating of activity instances, by associating meaning or semantics with raw source events. Typically, the ontology provides identifiers for the context and/or action, whereas the user and patient may be determined otherwise as discussed herein. The ontology may also provide, for the different activity types, classes, or definitions defined within the ontology, methods or functions that can be performed on or with respect each given activity type. For example, the generated clinical activity instance may include a timestamp, a location, and/or other fields. Also, note that while the subject field is typically bound to a patient, it could in other embodiments or circumstances be used to represent other types of persons (e.g., client, guest, customer) or things (e.g., medical imaging device, a room, a record).

Block 6103 includes storing the generated clinical activity instance. The clinical activity instance is stored, such as in the clinical activity network database 112. The clinical activity network addresses shortcomings in the prior art in various ways. First, the clinical activity network provides a history of activities occurring in the source healthcare system. In many environments, the source healthcare system does readily or at all represent such a history for many types of activities. For example, while a history of drugs administered may be represented, a history of room changes, nurse/doctor interactions, or other activities may not be represented in the source system. Second, the clinical activity network can be readily and without additional programming or processing be queried to answer questions such as who did what to whom when?

Figure 6B:
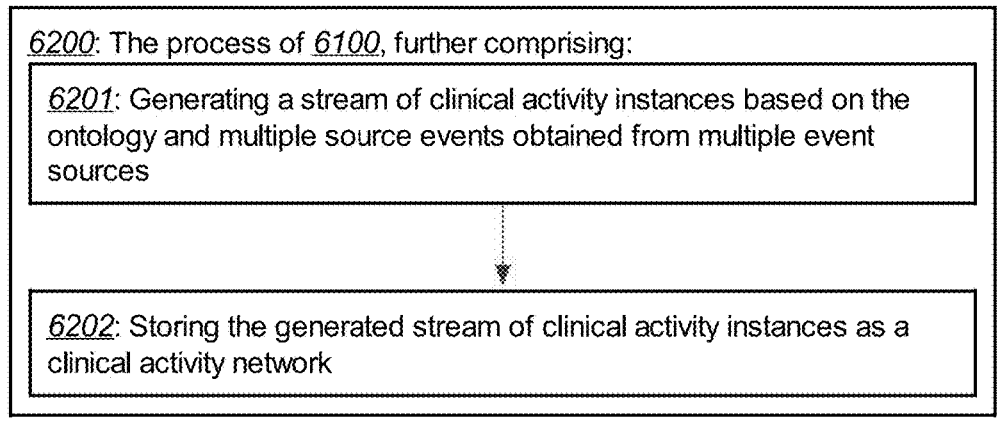

FIG. 6B is a flow diagram of example logic illustrating an extension of process 6100 of FIG. 6A. More particularly, FIG. 6B illustrates a process 6200 that includes the process 6100, and which further includes the following block(s).

Block 6201 includes generating a stream of clinical activity instances based on the ontology and multiple source events obtained from multiple event sources, wherein each of the event sources provides events in a distinct format. The multiple event sources may include a customer application, a customer database, a third-party application (e.g., fitness monitor), and the like. Typically, each of these sources will use a different format to represent the event, such as delimited text, XML, JSON, or the like.

Block 6202 includes storing the generated stream of clinical activity instances as a clinical activity network, wherein the clinical activity network represents a history of activities within the source healthcare system, and wherein the clinical activity network is configured to respond to a query that specifies one or more fields including a context, an action, a user, a subject, and a time, and that requests resolution of one or more the fields that are not specified by the query. The clinical activity network provides capabilities that are not present in the source healthcare system and its underlying data stores. In particular, the clinical activity network represents an accessible history of activities that can be queried and otherwise processed by applications or other clients. Example queries can ask questions such as who did what to whom when? For example, a query may specify a user and return all subjects (e.g., patients) who were the subject of some activity performed by the user during a particular timeframe. Another query could specify a patient and return all users who performed an activity on that patient. As a general matter, the clinical activity network may be configured to respond to a query that requests one or more clinical activities related to a specified user, patient, location, context, and/or time.

FIG. 6C is a flow diagram of example logic illustrating an extension of process 6100 of FIG. 6A. More particularly, FIG. 6C illustrates a process 6300 that includes the process 6100, wherein the generating, based on the source event and an activity ontology, a clinical activity instance includes the following block(s).

Block 6301 includes parsing the received source event to generate an activity pattern. As discussed above, the received source event (as data in text or another format) may be parsed or otherwise decomposed to determine a pattern or other structure.

Block 6302 includes matching the generated activity pattern against the activity ontology that associates activities with activity patterns. The matching may be performed against the ontology database 113. At a minimum, the matching may include matching identifiers that are associated with particular contexts represented in the ontology. In some cases, the matching may produce a set of multiple likely or potential contexts, such that multiple candidate matches are returned and processed further (with subsequent source events) to determine the actual context.

FIG. 6D is a flow diagram of example logic illustrating an extension of process 6100 of FIG. 6A. More particularly, FIG. 6D illustrates a process 6400 that includes the process 6100, wherein the generating, based on the source event and an activity ontology, a clinical activity instance includes the following block(s).

Block 6401 includes determining the user based on information external to the source event when the source event does not directly identify the user. In some cases, the source event may directly identify the user, such as by including a user identifier. When this is not the case, the process may determine the user by reference to external information. For example, the source event may include a process identifier, which can be used to determine the user with reference to a mapping of process identifiers to user identifiers. As another example, the process may determine the user with reference to a history of tracked log in and log out events, where those events are used to associate users with process or other identifiers found in the source events.

FIG. 6E is a flow diagram of example logic illustrating an extension of process 6400 of FIG. 6D. More particularly, FIG. 6E illustrates a process 6500 that includes the process 6400, wherein the determining the user based on information external to the source event includes the following block(s).

Block 6501 includes tracking log in and log out events. In some embodiments, a journal file or other type of data store tracks log in and log out events occurring on the source healthcare system. The journal file may include log in events that each associate a user identifier with a process identifier. Furthermore, the journal file may include log out events that indicate that a specified user has logged out.

Block 6502 includes generating an association between users and process identifiers based on the tracked events. The process generates a dynamic association that may be stored in a database or other repository, that tracks which process identifiers are associated with a given user at a particular time. The association may include historical information, or it may be a current state snapshot of the system.

Block 6503 includes determining the user by looking up the process identifier in the generated association. Generating and managing an association between process identifiers and users provides an important advantage in that it allows the platform to determine users even on systems that span multiple machines, or on systems where the platform does not have permission or access to process management data structures of the host operating system. In the multiple machine context, a process identifier may not be unique across machines, and there thus may be some ambiguity as to which user is associated with a given event.

FIG. 6F is a flow diagram of example logic illustrating an extension of process 6400 of FIG. 6D. More particularly, FIG. 6F illustrates a process 6600 that includes the process 6400, wherein the determining the user based on information external to the source event includes the following block(s).

Block 6601 includes determining a process identifier associated with the source event. The source event in some embodiments includes or references an identifier that references a process associated with the application that caused the source event to be generated.

Block 6602 includes determining the user by looking up the process identifier in an association between users and process identifiers, wherein the association tracks users that are logged into the source healthcare system and their associated processes. The determined process identifiers can be looked up in a table or other structure that maps process identifiers to users. This table may be stored by the operating system which hosts the application or database which generated the event.

FIG. 6G is a flow diagram of example logic illustrating an extension of process 6100 of FIG. 6A. More particularly, FIG. 6G illustrates a process 6700 that includes the process 6100, and which further includes the following block(s).

Block 6701 includes determining the action based on data content of the source event. Determining the action may include determining one or more action items, which identify an action/operation along with one or more data items. For example, an action may be to enter vitals for a patient, with a given blood pressure, heart rate, and temperature.

FIG. 6H is a flow diagram of example logic illustrating an extension of process 6100 of FIG. 6A. More particularly, FIG. 6H illustrates a process 6800 that includes the process 6100, and which further includes the following block(s).

Block 6801 includes receiving a second source event. Some embodiments employ a windowing technique, by receiving and processing multiple source events in order to determine a single activity instance. For example, an operation such as entering patient vitals may be distributed over two, three, or even more source events, such as a first event that identifies the application (e.g., a flow sheet application) and the patient, a second event that specifies a new blood pressure reading, a third event that specifies a new heart rate measurement, and so on.

Block 6802 includes determining at least one portion of a clinical activity instance based on the second source event. Here, the process may create a "partial" clinical activity instance, which is one that does not have all fields yet determined.

Block 6803 includes receiving a third source event after the second source event. In some cases, the process receives additional source events prior to receipt of the third event, where these additional events are not relevant to the current activity instance that is being generated. These additional events may be dropped or otherwise processed with respect to some other clinical activity instance. In general, the stream of source events includes interleaved events that are associated with many different patients. Thus, the process may concurrently generate multiple events corresponding to multiple patients or other subjects.

Block 6804 includes determining remaining fields of the clinical activity instance based on the third source event. The third event may include or be used to determine additional fields, such as action, location, or the like.

FIG. 6I is a flow diagram of example logic illustrating an extension of process 6100 of FIG. 6A. More particularly, FIG. 6I illustrates a process 6900 that includes the process 6100, and which further includes the following block(s).

Block 6901 includes determining a location associated with the source event. In some cases, the location may be determined by direct reference to the source event. More commonly, however, the location is determined with reference to state and history information that is tracked for users and/or patients. For example, some healthcare environments use tracking systems to track the location and movements of staff, patients, and/or equipment. Such tracking systems may be based on machine-readable indicia (e.g., active or passive RFID systems), smart mobile devices (e.g., smart phones with tracking/beacon apps), network location (e.g., from Wi-Fi routers), or the like. The process may reference the tracking system to determine the location of a particular clinical activity instance, by looking up the location of the user and/or the patient.

Figure 6J:
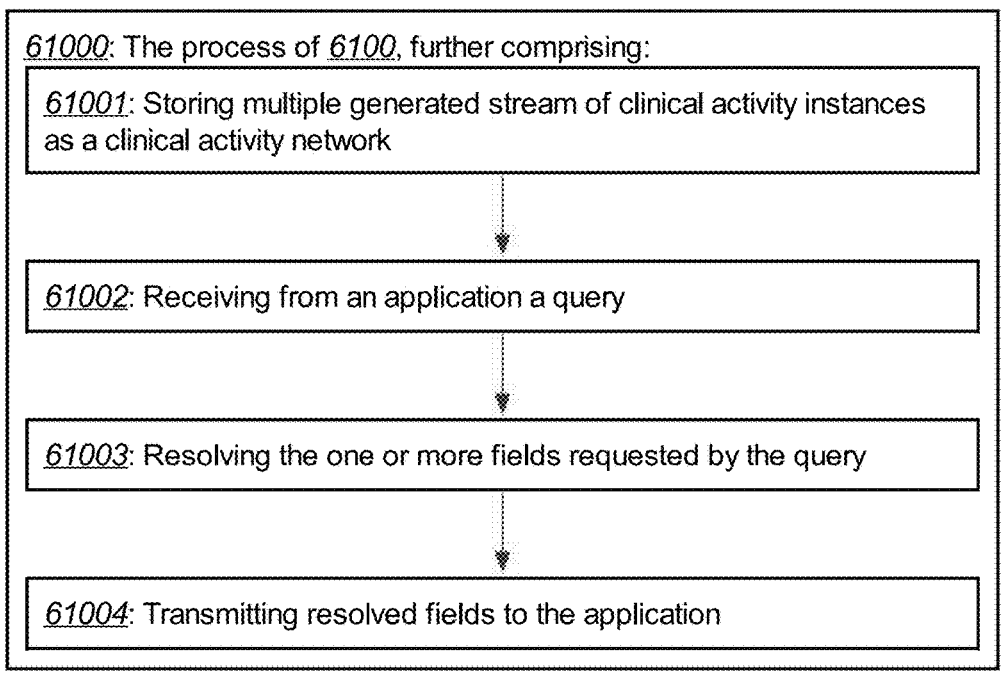

FIG. 6J is a flow diagram of example logic illustrating an extension of process 6100 of FIG. 6A. More particularly, FIG. 6J illustrates a process 61000 that includes the process 6100, and which further includes the following block(s).

Block 61001 includes storing multiple generated stream of clinical activity instances as a clinical activity network, wherein the clinical activity network represents a history of activities within the source healthcare system. As discussed above, the clinical activity network represents an accessible history of activities that can be queried and otherwise processed by applications or other clients. The clinical activity network is typically stored in a database or other representation that provides a relational access model for querying and accessing stored data.

Block 61002 includes receiving from an application a query that specifies one or more fields including a context, an action, a user, a subject, and a time, and that requests resolution of one or more the fields that are not specified by the query. The process may receive queries from various types of applications, including alert or early warning applications, relationship mining/mapping applications, process mining applications, or the like. Such queries typically specify one or more fields and request resolution of one or more other fields. Example queries can ask questions such as who did what to whom when? For example, a query may specify a user and return all subjects (e.g., patients) who were the subject of some activity performed by the user during a particular timeframe. Another query could specify a patient and return all users who performed an activity on that patient.

Block 61003 includes resolving the one or more fields requested by the query. Resolving the fields may include processing a query in a relational database that stores the clinical activity network.

Block 61004 includes transmitting resolved fields to the application. Once the fields and/or other data has been resolved, it is transmitted to the application for further use, such as additional processing, display, or the like.

4. Access

As noted above, some embodiments provide a relational access model to the extracted data stored in the clinical data engine. In some contexts, the source customer data may be represented in a hierarchical data format. For example, the source customer data may be electronic health records that are represented in a B-tree format. The B-tree format is naturally suited to storing sparse, key-value data such as may be present in the electronic health records context. As also noted above, in at least the case of MUMPS, the source customer data may not support or provide a relational access model, such as is provided by modern SQL-based relational database systems.

Some embodiments provide relational access by initially storing the extracted data in a Log-Structured Merge ("LSM") format. The LSM format is a tree-based format that can efficiently represent sparse key-value data, such as is common in the health records context. In addition the LSM format allows for the storage of data contiguously on disk, making it ideal for recollecting data about a given data topic, such as Patient medications history. Example LSM-based storage systems include RocksDB, SQLite, and Level DB. In some embodiments, such a storage system is used to implement all or part of the clinical data engine 114 of FIG. 1A.

Storing the extracted data in an LSM format may include translating the extracted data from its native B-tree format into a corresponding representation for the LSM-based data store. To accomplish the translation between data stored in a B-tree format and the LSM store, the following steps are taken when a data item is copied from the source customer data to the clinical data engine. First, the incoming data item is parsed from its native (e.g., MUMPS-based) representation and divided into the items subscripts (keys) and corresponding values. The data item is typically a portion of a patient health record, such as patient contact information, patient location, a lab result, medication, a measurement (e.g., blood pressure, temperature), or the like. Second, type inference is performed for each subscript, so that an LSM-based key can be constructed for the data item. Third, the typed subscripts and corresponding values are encoded to create a respective LSM-based key and value. Finally, the key-value pair is stored in the LSM-based data store. A similar approach may be employed when reading data from the LSM-based data store given a key represented in the B-tree format. Such a read operation may be performed by the above-described extraction processes to determine whether a given item has already been extracted and is thus already present in the LSM-based data store.

Once the data is stored in the LSM-based data store, the OIP 100 can provide relational access to the stored data by performing on-the-fly translation of SQL queries/commands into corresponding access commands for the LSM-based data store. For example, a SQL query may be converted into a series of operations that traverse the LSM-based data store in order to retrieve the resulting data set specified by the SQL query. Some embodiments provide a virtual table that can be accessed by a SQL client. To a SQL client, the virtual table behaves like any other table, but internally, the virtual table invokes callbacks to perform functions against the underlying LSM-tree. Thus, a SQL query on or with respect to the virtual table results in one or more LSM-tree access operations that are performed to satisfy the constraints specified by the SQL query.

5. Example Computing System Implementation

Figure 7:
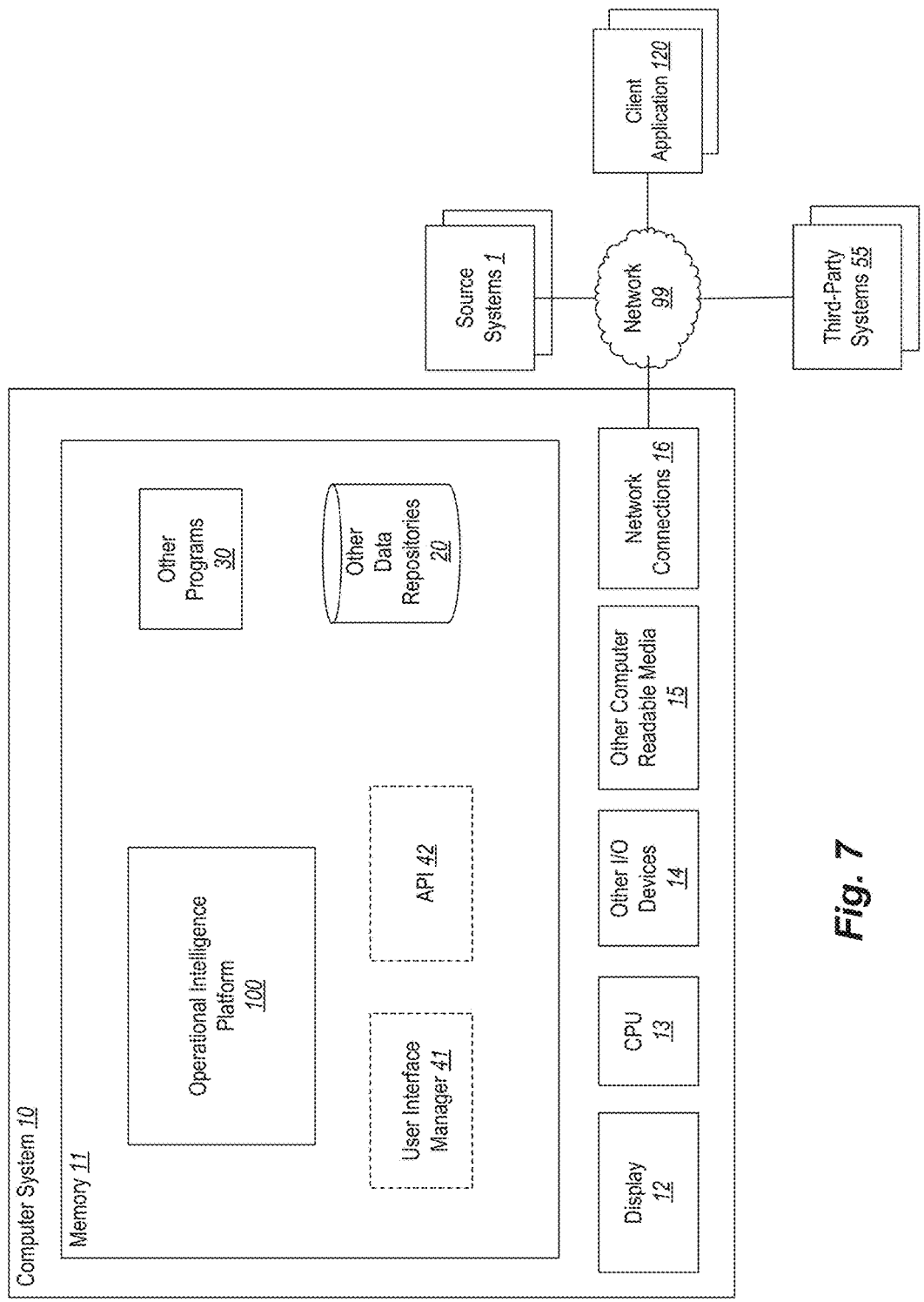
FIG. 7 is a block diagram of a computing system for implementing an operational intelligence platform according to an example embodiment.

FIG. 7 is a block diagram of a computing system for implementing an operational intelligence platform according to an example embodiment. In particular, FIG. 3 shows a computing system 10 that may be utilized to implement an OIP 100.

Note that one or more general purpose or special purpose computing systems/devices may be used to implement the OIP 100. In addition, the computing system 10 may comprise one or more distinct computing systems/devices and may span distributed locations. Furthermore, each block shown may represent one or more such blocks as appropriate to a specific embodiment or may be combined with other blocks. Also, the OIP 100 may be implemented in software, hardware, firmware, or in some combination to achieve the capabilities described herein.

In the embodiment shown, computing system 10 comprises a computer memory ("memory") 11, a display 12, one or more Central Processing Units ("CPU") 13, Input/Output devices 14 (e.g., keyboard, mouse, CRT or LCD display, and the like), other computer-readable media 15, and network connections 16. The OIP 100 is shown residing in memory 11. In other embodiments, some portion of the contents, some or all of the components of the OIP 100 may be stored on and/or transmitted over the other computer-readable media 15. The components of the OIP 100 preferably execute on one or more CPUs 13 and perform the techniques described herein. Other code or programs 30 (e.g., an administrative interface, a Web server, and the like) and potentially other data repositories, such as data repository 20, also reside in the memory 11, and preferably execute on one or more CPUs 13. Of note, one or more of the illustrated components may not be present in any specific implementation. For example, some embodiments may not provide other computer-readable media 15 or a display 12.

The OIP 100 is shown executing in the memory 11 of the computing system 10. Also included in the memory are a user interface manager 41 and an application program interface ("API") 42. The user interface manager 41 and the API 42 are drawn in dashed lines to indicate that in other embodiments, functions performed by one or more of these components may be performed externally to the system that hosts the OIP 100.

The UI manager 41 provides a view and a controller that facilitate user interaction with the OIP 100 and its various components. For example, the UI manager 41 may provide interactive access to the OIP 100, such that users can interact with the OIP 100, such as by providing a graphical user interface that is configured to facilitate control and management of the OIP 100. In some embodiments, access to the functionality of the UI manager 41 may be provided via a Web server, possibly executing as one of the other programs 30. In such embodiments, a user operating a Web browser executing on one of the client devices 50 can interact with the OIP 100 via the UI manager 41.

The API 42 provides programmatic access to one or more functions of the OIP 100. For example, the API 42 may provide a programmatic interface to one or more functions of the OIP 100 that may be invoked by one of the other programs 30 or some other module. In this manner, the API 42 facilitates the development of third-party software, such as user interfaces, plug-ins, adapters (e.g., for integrating functions of the OIP 100 into Web applications), and the like.

In addition, the API 42 may be in at least some embodiments invoked or otherwise accessed via remote entities, such as code executing on one of the source systems 1, client applications 120, and/or third-party systems 55, to access various functions of the OIP 100. For example, the source system 1 may push records and/or data updates to the OIP 100 via the API 42. As another example, the client application 120 may query information hosted by the OIP via the API 42. The API 42 may also be configured to provide management widgets (e.g., code modules) that can be integrated into the third-party systems 55 and that are configured to interact with the OIP 100 to make at least some of the described functionality available within the context of other applications (e.g., mobile apps).

The OIP 100 interacts via the network 99 with source systems 1, client applications 120, and third-party systems/applications 55. The network 99 may be any combination of media (e.g., twisted pair, coaxial, fiber optic, radio frequency), hardware (e.g., routers, switches, repeaters, transceivers), and protocols (e.g., TCP/IP, UDP, Ethernet, Wi-Fi, WiMAX) that facilitate communication between remotely situated humans and/or devices. The third-party systems/applications 55 may include any systems that provide data to, or utilize data from, the OIP 100, including Web browsers, messaging systems, supplemental data sources, backup systems, and the like.

In an example embodiment, components/modules of the OIP 100 are implemented using standard programming techniques. For example, the OIP 100 may be implemented as a "native" executable running on the CPU 13, along with one or more static or dynamic libraries. In other embodiments, the OIP 100 may be implemented as instructions processed by a virtual machine that executes as one of the other programs 30. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., Scala, ML, Lisp, Scheme, and the like), procedural (e.g., C, Pascal, Ada, Modula, and the like), scripting (e.g., Perl, Ruby, Python, JavaScript, VBScript, and the like), and declarative (e.g., SQL, Prolog, and the like).

The embodiments described above may also use either well-known or proprietary synchronous or asynchronous client-server computing techniques. Also, the various components may be implemented using more monolithic programming techniques, for example, as an executable running on a single CPU computer system, or alternatively decomposed using a variety of structuring techniques known in the art, including but not limited to, multiprogramming, multithreading, client-server, or peer-to-peer, running on one or more computer systems each having one or more CPUs. Some embodiments may execute concurrently and asynchronously, and communicate using message passing techniques. Equivalent synchronous embodiments are also supported. Also, other functions could be implemented and/or performed by each component/module, and in different orders, and by different components/modules, yet still achieve the described functions.

In addition, programming interfaces to the data stored as part of the OIP 100, such as in the configuration data 112, clinical data engine 114, and/or the other data repositories 20, can be available by standard mechanisms such as through C, C++, C#, and Java APIs; libraries for accessing files, databases, or other data repositories; through scripting languages such as XML; or through Web servers, FTP servers, or other types of servers providing access to stored data. The configuration data 112, clinical data engine 114, and the other data repositories 20 may be implemented as one or more database systems, file systems, or any other technique for storing such information, or any combination of the above, including implementations using distributed computing techniques.

Different configurations and locations of programs and data are contemplated for use with techniques of described herein. A variety of distributed computing techniques are appropriate for implementing the components of the illustrated embodiments in a distributed manner including but not limited to TCP/IP sockets, RPC, RMI, HTTP, Web Services (XML-RPC, JAX-RPC, SOAP, and the like). Other variations are possible. Also, other functionality could be provided by each component/module, or existing functionality could be distributed amongst the components/modules in different ways, yet still achieve the functions described herein.

Furthermore, in some embodiments, some or all of the components of the OIP 100 may be implemented or provided in other manners, such as at least partially in firmware and/or hardware, including, but not limited to one or more application-specific integrated circuits ("ASICs"), standard integrated circuits, controllers executing appropriate instructions, and including microcontrollers and/or embedded controllers, field-programmable gate arrays ("FPGAs"), complex programmable logic devices ("CPLDs"), and the like. Some or all of the system components and/or data structures may also be stored as contents (e.g., as executable or other machine-readable software instructions or structured data) on a computer-readable medium (e.g., as a hard disk; a memory; a computer network or cellular wireless network or other data transmission medium; or a portable media article to be read by an appropriate drive or via an appropriate connection, such as a DVD or flash memory device) so as to enable or configure the computer-readable medium and/or one or more associated computing systems or devices to execute or otherwise use or provide the contents to perform at least some of the described techniques. Some or all of the components and/or data structures may be stored on tangible, non-transitory storage mediums. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

All of the above U.S. patents, U.S. patent application publications, U.S. patent applications, foreign patents, foreign patent applications, non-patent publications, and appendixes referred to in this specification and/or listed in the Application Data Sheet are incorporated herein by reference, in their entireties.

While specific embodiments of the invention have been illustrated and described, as noted above, many changes can be made without departing from the spirit and scope of the invention. Accordingly, the scope of the invention is not limited by the disclosure of the above-described embodiments. Instead, the invention should be determined entirely by reference to the claims.

The invention claimed is:

1. A method for generating a clinical activity network, the method comprising:
   receiving a source event that represents a database update event or an application event caused by an activity performed in a source healthcare system;
   generating, based on the source event and an activity ontology, a clinical activity instance that identifies a context, an action, a user, and a subject;
   storing the generated clinical activity instance;
   generating a stream of clinical activity instances by performing real-time extraction of data stored in a source database, wherein the data is obtained from a journal file that includes updates to the source database that are based on write operations performed by a customer application to store the data in the source database, wherein the write operations are performed by the customer application in response to user interface events, application-level events/operations, and/or data access events/operations occurring with respect to the customer application, wherein the write operations cause the data to be stored in the journal file before it is written to the source database;
   storing multiple generated streams of clinical activity instances as a clinical activity network, wherein the clinical activity network represents a history of activities within the source healthcare system;
   receiving from an application a query that specifies one or more fields including a context, an action, a user, a subject, and a time, and that requests resolution of one or more the fields that are not specified by the query;
   resolving the one or more fields requested by the query; and
   transmitting resolved fields to the application.

2. The method of claim 1, further comprising:
   generating a stream of clinical activity instances based on the ontology and multiple source events obtained from multiple event sources, wherein each of the event sources provides events in a distinct format; and
   storing the generated stream of clinical activity instances as a clinical activity network, wherein the clinical activity network represents a history of activities within the source healthcare system, and wherein the clinical activity network is configured to respond to a query that specifies one or more fields including a context, an action, a user, a subject, and a time, and that requests resolution of one or more the fields that are not specified by the query.

3. The method of claim 1, wherein the generating, based on the source event and an activity ontology, a clinical activity instance includes:
   parsing the received source event to generate an activity pattern; and
   matching the generated activity pattern against the activity ontology that associates activities with activity patterns.

4. The method of claim 1, wherein the receiving a source event includes: receiving text data that represents an application event associated with an operation of a user performed with respect to a customer application, the text data referencing the user, the application, and the performed operation.

5. The method of claim 1, wherein the receiving a source event includes: receiving text data that represents a database update event associated with an update to a customer database that is based on a write operation performed by a customer application to store the data in the source database.

6. The method of claim 1, wherein the generating, based on the source event and an activity ontology, a clinical activity instance includes: determining the user based on information external to the source event when the source event does not directly identify the user.

7. The method of claim 6, wherein the determining the user based on information external to the source event includes:
   tracking log in and log out events;
   generating an association between users and process identifiers based on the tracked events; and
   determining the user by looking up the process identifier in the generated association.

8. The method of claim 6, wherein the determining the user based on information external to the source event includes:
   determining a process identifier associated with the source event; and
   determining the user by looking up the process identifier in an association between users and process identifiers, wherein the association tracks users that are logged into the source healthcare system and their associated processes.

9. The method of claim 1, further comprising: determining the action based on data content of the source event.

10. The method of claim 1, further comprising:
    receiving a second source event;
    determining at least one portion of a clinical activity instance based on the second source event;
    receiving a third source event after the second source event; and
    determining remaining fields of the clinical activity instance based on the third source event.

11. The method of claim 10, further comprising:
    receiving one or more additional source events between receipt of the second and third source events;
    determining that the one or more additional source events are not relevant to the clinical activity instance; and
    dropping the one or more additional source events.

12. The method of claim 1, further comprising: determining a location associated with the source event.

13. A system for generating a clinical activity network, the system comprising:
a processor;
a memory; and
a operational intelligence platform module that is stored in the memory and that is configured, when executed by the processor, to perform:
receiving a source event that represents a database update event or an application event caused by an activity performed in a source healthcare system;
generating, based on the source event and an activity ontology, a clinical activity instance that identifies a context, an action, a user, and a subject;
storing the generated clinical activity instance in the clinical activity network;
generating a stream of clinical activity instances by performing real-time extraction of data stored in a source database, wherein the data is obtained from a journal file that includes updates to the source database that are based on write operations performed by a customer application to store the data in the source database, wherein the write operations are performed by the customer application in response to user interface events, application-level events/operations, and/or data access events/operations occurring with respect to the customer application, wherein the write operations cause the data to be stored in the journal file before it is written to the source database;
storing multiple generated streams of clinical activity instances as a clinical activity network, wherein the clinical activity network represents a history of activities within the source healthcare system;
receiving from an application a query that specifies one or more fields including a context, an action, a user, a subject, and a time, and that requests resolution of one or more the fields that are not specified by the query;
resolving the one or more fields requested by the query; and
transmitting resolved fields to the application.

14. The system of claim 13, wherein the source event is obtained by a journal file of the source healthcare system, the journal file storing updates to a database containing electronic health records managed by the source heath care system.

15. The system of claim 13, wherein the operational intelligence platform is further configured to: generate and store a stream of clinical activity instances in the clinical activity network, wherein the clinical activity network represents a history of activities within the source healthcare system.

16. The system of claim 15, wherein the clinical activity network is configured to respond to a query that specifies one or more fields including a context, an action, a user, a subject, and a time, and that requests resolution of one or more the fields that are not specified by the query.

17. The system of claim 15, wherein the clinical activity network is configured to respond to a query that requests one or more clinical activities related to a specified user, patient, location, context, and/or time.

18. A non-transitory computer-readable medium including contents that are configured, when executed, to cause a computing system to perform a method for generating a clinical activity network, the method comprising:
receiving a source event that represents a database update event or an application event caused by an activity performed in a source healthcare system;
generating, based on the source event and an activity ontology, a clinical activity instance that identifies a context, an action, a user, and a subject;
storing the generated clinical activity instance;
generating a stream of clinical activity instances by performing real-time extraction of data stored in a source database, wherein the data is obtained from a journal file that includes updates to the source database that are based on write operations performed by a customer application to store the data in the source database, wherein the write operations are performed by the customer application in response to user interface events, application-level events/operations, and/or data access events/operations occurring with respect to the customer application, wherein the write operations cause the data to be stored in the journal file before it is written to the source database;
storing multiple generated streams of clinical activity instances as a clinical activity network, wherein the clinical activity network represents a history of activities within the source healthcare system;
receiving from an application a query that specifies one or more fields including a context, an action, a user, a subject, and a time, and that requests resolution of one or more the fields that are not specified by the query;
resolving the one or more fields requested by the query; and
transmitting resolved fields to the application.

19. The system of claim 13, further comprising multiple parsers that are each configured to:
receive text data from a corresponding data stream that provides indications of application actions, database operations, or system notifications;
parse, based on a predefined pattern matching expression, the received text data into a parse data structure that includes an activity identifier and a subject identifier that identifies a person who is the subject of the activity;
provide the activity identifier and the subject identifier to a generator module that creates a clinical activity instance based on the activity identifier and the subject identifier together with a user identifier.

20. The system of claim 19, wherein the first one of the multiple parsers receives data from the source database, wherein a second one of the multiple parsers receives data based on user interface events in a source customer application, wherein a third one of the multiple parsers receives data based on events occurring in a personal fitness or health monitoring device.

* * * * *